US008211659B2

(12) United States Patent
Jiang et al.

(10) Patent No.: US 8,211,659 B2
(45) Date of Patent: Jul. 3, 2012

(54) METHODS AND KITS FOR DETECTION OF CANCER METASTASIS

(75) Inventors: Ming-Chung Jiang, Wuci Township (TW); Chin-Shaw Stella Tsai, Wuci Township (TW); Min-Che Tung, Wuci Township (TW); Jai-Nien Tung, Wuci Township (TW)

(73) Assignees: Tungs' Taichung Metroharbor Hospital, Wuci Township (TW); Ming-Chung Jiang, Wuci Township (TW)

( * ) Notice: Subject to any disclaimer, the term of this patent is extended or adjusted under 35 U.S.C. 154(b) by 377 days.

(21) Appl. No.: 12/267,395

(22) Filed: Nov. 7, 2008

(65) Prior Publication Data

US 2010/0120074 A1    May 13, 2010

(51) Int. Cl.
*G01N 33/574* (2006.01)
(52) U.S. Cl. ........................................ 435/7.23; 435/7.1
(58) Field of Classification Search .................... None
See application file for complete search history.

(56) References Cited

U.S. PATENT DOCUMENTS

| | | | |
|---|---|---|---|
| 5,759,782 A | 6/1998 | Pastan et al. | |
| 6,072,031 A | 6/2000 | Pastan et al. | |
| 6,156,564 A | 12/2000 | Pastan et al. | |
| 6,207,380 B1 | 3/2001 | Billing-Medel et al. | |
| 6,232,086 B1 | 5/2001 | Pastan et al. | |
| 6,440,737 B1 | 8/2002 | Freier | |
| 6,664,057 B2 | 12/2003 | Albertson et al. | |
| 2005/0260639 A1* | 11/2005 | Nakamura et al. | 435/6 |
| 2008/0081339 A1* | 4/2008 | Liu et al. | 435/6 |
| 2008/0248501 A1* | 10/2008 | LePage et al. | 435/7.23 |

FOREIGN PATENT DOCUMENTS

WO    WO 2009/052573    *    4/2009

OTHER PUBLICATIONS

Tockman et al, Cancer Res., 1992, 52:2711s-2718s.*
Liao, C.F., et al., "CSE1L/CAS, the cellular apoptosis susceptibility protein, enhances invasion and metastasis but not proliferation of cancer cells," J. Exp. Clin. Cancer Res., 2008, 27(15), 12 pages.
Basuyau JP, Leroy M, Brunelle P. (2001) Determination of tumor markers in serum. Pitfalls and good practice. Clin Chem Lab Med 39: 1227-1233.
Behrens P, Brinkmann U, Fogt F, Wernert N, Wellmann A. (2001) Implication of the proliferation and apoptosis associated CSEIL/CAS gene for breast cancer development. Anticancer Res 21: 2413-2417.
Behrens P, Brinkmann U, Wellmann A. (2003) CSEIL/CAS: its role in proliferation and apoptosis. Apoptosis 8: 39-44.
Bogenrieder T, Herlyn M. (2003). Axis of evil: Molecular mechanisms of cancer metastasis. Oncogene 22: 6524-6536.
Boni R, Wellmann A, Man YG, Hofbauer G, Brinkmann U. (1999) Expression of the proliferation and apoptosis-associated CAS protein in benign and malignant cutaneous melanocytic lesions. Am J Dermatopathol 21: 125-128.
Brandtzaeg P, Bjerke K, Kett K, Kvale D, Rognum TO, Scott H, Sollid LM, Valnes K. (1987) Production and secretion of immunoglobulins in the gastrointestinal tract. Ann Allergy 59: 21-39.
Brenner DE, Normolle DP. (2007) Biomarkers for cancer risk, early detection, and prognosis: the validation conundrum. Cancer Epidemiol Biomarkers Prev 16: 1918-1920.
Bresalier RS, Byrd JC, Tessler D, Lebel J, Koomen J, Hawke D, Half E, Liu KF, Mazurek N; Great Lakes-New England Clinical and Epidemiology Center of the Early Detection Research Network. (2004) A circulating ligand for galectin-3 is a haptoglobin-related glycoprotein elevated in individuals with colon cancer. Gastroenterology 127: 741-748.
Breslow RA, Sorkin JD, Frey CM, Kessler LG. (1997) Americas' knowledge of cancer risk and survival. Prev Med 26: 170-177.
Brinkmann U, Brinkmann E, Pastan I. (1995a) Expression cloning of cDNAs that renders cancer cells resistant to *Pseudomonas* and dephtheria toxin and immunotoxins. Mol Med 1: 206-216.
Brinkmann U, Brinkmann E, Gallo M, Pastan I. (1995b) Cloning and characterization of a cellular apoptosis susceptibility gene, the human homologue to the yeast chromosome segregation gene CSE1. Proc Natl Acad Sci USA 92:10427-10431.
Chu DZJ, Erickson CA, Russell MP, Thompson C, Lang NP, Broadwater RJ, Westbrook KC. (1991). Prognostic significance of carcinoembryonic antigen in colorectal carcinoma. Arch Surg 126: 314-316.
Fong S, Garcia Vega G, León V. (1985) Carcinoembryonic antigen fraction in digestive cancer. Neoplasma 32: 199-208.
Go VL. (1976) Carcinoembryonic antigen: clinical application. Cancer 37: 562-566.
Gold P. Freedman S.O. (1965) Specific carcinoembryonic antigens of the human digestive system. J. Exp. Med. 122: 467-481.
Gupta AK, Brenner DE, Turgeon DK. (2008) Early detection of colon cancer: new tests on the horizon. Mol Diagn Ther. 12: 77-85.
Hammarström S. (1999) The carcinoembryonic antigen (CEA) family: structures, suggested functions and expression in normal and malignant tissues. Sem. Cancer Biol. 9: 67-81.
Holmbeck K, Bianco P, Yamada S, Birkedal-Hansen H. (2004) MT1-MMP: a tethered collagenase. J Cell Physiol 200: 11-19.
Hsu TC. (2006) Unusual elevation of CEA in a patient with history of colon cancer. Jpn J Clin Oncol. 36: 811-813.
Izaguirre MF, Vergara MN, Casco VH. (2006) CAS role in the brain apoptosis of *Bufo arenarum* induced by cypermethrin. Biocell 30: 309-320.
Jena BP. (2005) Molecular machinery and mechanism of cell secretion. Exp Biol Med (Maywood) 230: 307-319.
Jiang MC, Luo SF, Li LT, Lin CC, Du SY, Lin CY, Liao CF. (2007) Synergic CSE1L/CAS, TNFR-1, and p53 apoptotic pathways in combined interferon-gamma/adriamycin-induced apoptosis of Hep G2 hepatoma cells. J Exp Clin Cancer Res 26: 91-99.

(Continued)

*Primary Examiner* — Misook Yu
*Assistant Examiner* — Mark Halvorson
(74) *Attorney, Agent, or Firm* — McDonnell Boehnen Hulbert & Berghoff LLP

(57) ABSTRACT

The invention provides a method of detecting metastasis of cancers in the body fluids from a mammal, the method comprising the steps of: (a) providing the body fluids from the mammal; and (b) the measurement of the CAS protein level or CAS polypeptide level in the body fluids to screen or diagnose the metastatic cancers.
Also provided is a kit for the method of the invention.

11 Claims, 10 Drawing Sheets

OTHER PUBLICATIONS

Figure 1:
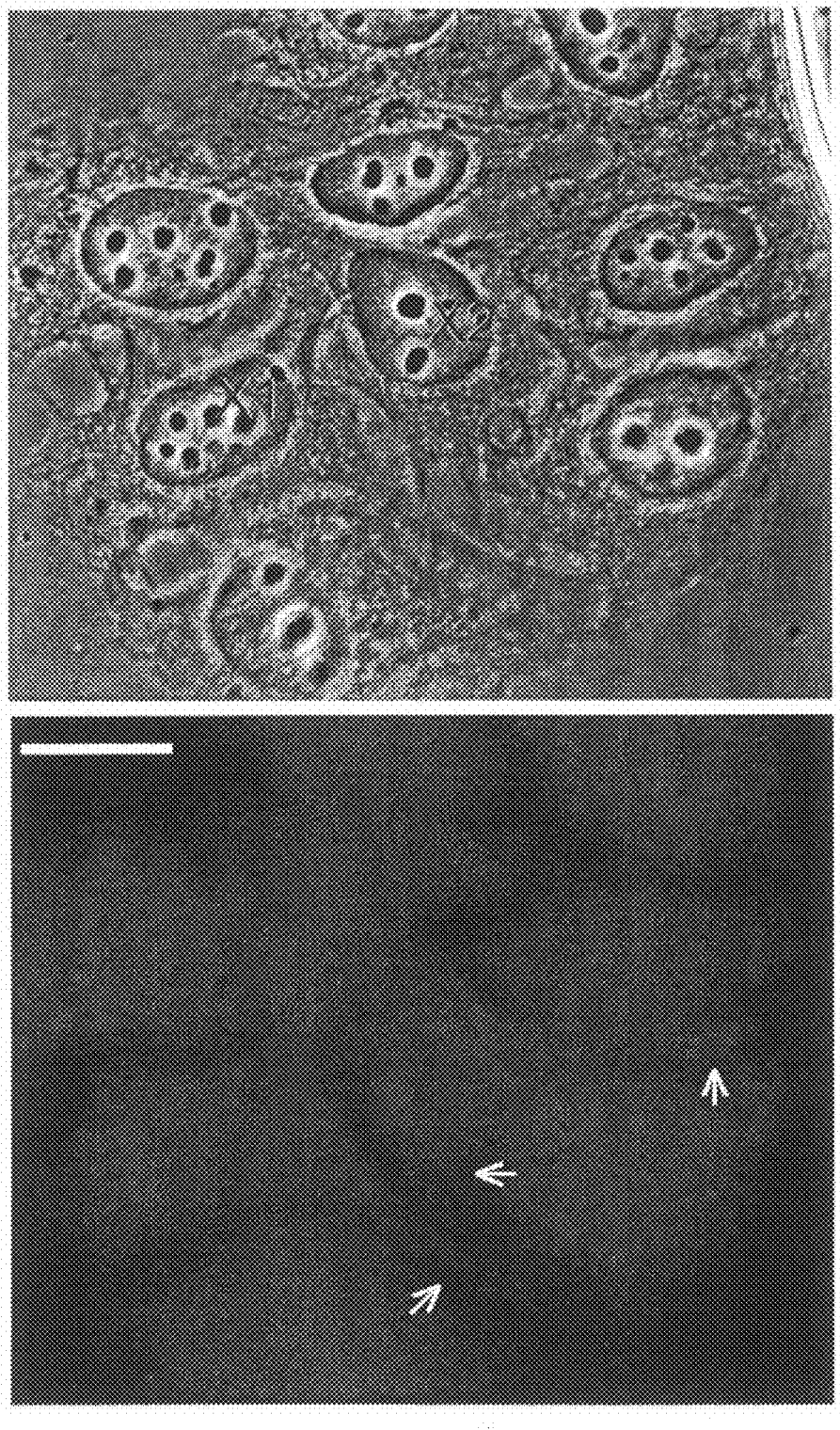

23. [0090] Kutay U, Bischoff FR, Kostka S, Kraft R, Gorlich D. (1997) Export of importin alpha from the nucleus is mediated by a specific nuclear transport factor. Cell 90: 1061-1071.

Kwan JA, Schulze CJ, Wang W, Leon H, Sariahmetoglu M, Sung M, Sawicka J, Sims DE, Sawicki G, Schulz R. (2004) Matrix metalloproteinase-2 (MMP-2) is present in the nucleus of cardiac myocytes and is capable of cleaving poly (ADP-ribose) polymerase (PARP) in vitro. FASEB J 18: 690-692.

Lassmann S, Tang L, Capanu M, Brabletz T, Schöpflin A, Zur Hausen A, Gonen M, Kemeny N, Shia J, Klimstra D, Werner M. (2007) Predictive molecular markers for colorectal cancer patients with resected liver metastasis and adjuvant chemotherapy. Gastroenterology. 133: 1831-1839.

Lee DC, Chua DT, Wei WI, Sham JS, Lau AS. (2007) Induction of matrix metalloproteinases by Epstein-Barr virus latent membrane protein 1 isolated from nasopharyngeal carcinoma. Biomed Pharmacother 61: 520-526.

Liao CF, Luo SF, Tsai CS, Tsao TY, Chen SL, Jiang MC. (2008a) CAS enhances chemotherapeutic drug-induced p53 accumulation and apoptosis: use of CAS for high-sensitivity anticancer drug screening, Toxicol. Mech. Method. In press, DOI: 10.1080/15376510802428609.

Liao CF, Luo SF, Shen TY, Lin CH, Chien JT, Du SY, Jiang MC. (2008b) CSE1L/CAS, a microtubule-associated protein, inhibits taxol (paclitaxel)-induced apoptosis but enhances cancer cell apoptosis induced by various chemotherapeutic drugs. BMB Rep 41: 210-216.

Liao CF, Luo SF, Li LT, Lin CY, Chen YC, Jiang MC. (2008c) CSE1L/CAS, the cellular apoptosis susceptibility protein, enhances invasion and metastasis but not proliferation of cancer cells. J Exp Clin Cancer Res 27: 15. doi: 10.1186/1756-9966-27-15.

Moertel CG, Fleming TR, Macdonald JS, Haller DG, Laurie JA, Tangen C. (1993) An evaluation of the carcinoembryonic antigen (CEA) test for monitoring patients with resected colon cancer. JAMA. 270: 943-947.

Moser TL, Young TN, Rodriguez GC, Pizzo SV, Bast RC Jr, Stack MS. (1994) Secretion of extracellular matrix-degrading proteinases is increased in epithelial ovarian carcinoma. Int J Cancer 56: 552-559.

Nguyen M, Arkell J, Jackson CJ. (1998) Active and tissue inhibitor of matrix metalloproteinase-free gelatinase B accumulates within human microvascular endothelial vesicles. J Biol Chem 273: 5400-5404.

Peiro G, Diebold J, Baretton GB, Kimmig R, Lohrs U. (2001) Cellular apoptosis susceptibility gene expression in endometrial carcinoma: correlation with Bcl-2, Bax, and caspase-3 expression and outcome. Int J Gynecol Pathol 20: 359-367.

Petricoin EF, Belluco C, Araujo RP, Liotta LA. (2006) The blood peptidome: a higher dimension of information content for cancer biomarker discovery. Nat Rev Cancer 6: 961-967.

Pickett JA, Edwardson JM. (2006) Compound exocytosis: mechanisms and functional significance. Traffic 7: 109-116.

Pieper-Bigelow C, Strocchi A, Levitt MD. (1990) Where does serum amylase come from and where does it go? Gastroenterol. Clin. North. Am. 19: 793-810.

Ransohoff DF, Martin C, Wiggins WS, Hitt BA, Keku TO, Galanko JA, Sandler RS. (2008) Assessment of serum proteomics to detect large colon adenomas. Cancer Epidemiol Biomarkers Prev. 17: 2188-2193.

Rex DK, Kahi CJ, Levin B, Smith RA, Bond JH, Brooks D, Burt RW, Byers T, Fletcher RH, Hyman N, Johnson D, Kirk L, Lieberman DA, Levin TR, O'Brien MJ, Simmang C, Thorson AG, Winawer SJ; American Cancer Society; US Multi-Society Task Force on Colorectal Cancer. (2006) Guidelines for colonoscopy surveillance after cancer resection: a consensus update by the American Cancer Society and the US Multi-Society Task Force on Colorectal Cancer. Gastroenterology. 130: 1865-1871.

Rodrigues LR, Teixeira JA, Schmitt FL, Paulsson M, Lindmark-Mänsson H. (2007) The role of osteopontin in tumor progression and metastasis in breast cancer. Cancer Epidemiol Biomarkers Prey 16: 1087-1097.

Saito N, Kameoka S. (2005) Serum laminin is an independent prognostic factor in colorectal cancer. Int J Colorectal Dis. 20: 238-244.

Savrin RA, Cooperman M, Martin EW Jr. (1979) Clinical application of carcinoembryonic antigen in patients with colorectal carcinoma. Dis Colon Rectum. 22: 211-215.

Scherf U, Pastan I, Willingham MC, Brinkmann U. (1996) The human CAS protein which is homologous to the CSE1 yeast chromosome segregation gene product is associated with microtubules and mitotic spindle. Proc Natl Acad Sci U S A. Apr. 2;93(7):2670-2674.

Seiden-Long IM, Brown KR, Shih W, Wigle DA, Radulovich N, Jurisica I et al. (2006) Transcriptional targets of hepatocyte growth factor signalling and Ki-ras oncogene activation in colorectal cancer. Oncogene 25: 91-102.

Shields JD, Emmett MS, Dunn DB, Joory KD, Sage LM, Rigby H et al. (2007) Chemokine-mediated migration of melanoma cells towards lymphatics: a mechanism contributing to metastasis. Oncogene 26: 2997-3005.

Skates SJ, Horick NK, Moy JM, Minihan AM, Seiden MV, Marks JR, Sluss P, Cramer DW. (2007) Pooling of case specimens to create standard serum sets for screening cancer biomarkers. Cancer Epidemiol Biomarkers Prey 16: 334-341.

Stein U, Arlt F, Walther W, Smith J, Waldman T, Harris ED, Mertins SD, Heizmann CW, Allard D, Birchmeier W, Schlag PM, Shoemaker RH. (2006) The metastasis-associated gene S100A4 is a novel target of beta-catenin/T-cell factor signaling in colon cancer. Gastroenterology. 131: 1486-1500.

Stetler-Stevenson WG, Aznavoorian S, Liotta LA. (1993) Tumor cell interactions with the extracellular matrix during invasion and metastasis. Annu Rev Cell Biol 9: 541-573.

Taraboletti G, Sonzogni L, Vergani V, Hosseini G, Ceruti R, Ghilardi C et al. (2000) Posttranscriptional stimulation of endothelial cell matrix metalloproteinases 2 and 1 by endothelioma cells. Exp Cell Res 258: 384-394.

Thomas CM, Sweep CG. (2001) Serum tumor markers: past, state of the art, and future. Int J Biol Markers 16: 73-86.

Thomson DM, Krupey J, Freedman SO, Gold P. (1969) The radioimmunoassay of circulating carcinoembryonic antigen of the human digestive system. Proc Natl Acad Sci USA 64: 161-167.

Wang H, Li M, Lin W, Wang W, Zhang Z, Rayburn ER, Lu J, Chen D, Yue X, Shen F, Jiang F, He J, Wei W, Zeng X, Zhang R. (2007) Extracellular activity of cyclic AMP-dependent protein kinase as a biomarker for human cancer detection: distribution characteristics in a normal population and cancer patients. Cancer Epidemiol Biomarkers Prey 16: 789-795.

Wellmann A, Flemming P, Behrens P, Wuppermann K, Lang H, Oldhafer K et al. (2001) High expression of the proliferation and apoptosis associated CSE1L/CAS gene in hepatitis and liver neoplasms: correlation with tumor progression. Int J Mol Med 7: 489-494.

Wellmann A, Krenacs L, Fest T, Scherf U, Pastan I, Raffeld M et al. (1997) Localization of the cell proliferation and apoptosis-associated CAS protein in lymphoid neoplasms. Am J Pathol 150: 25-30.

Zhang H, Chan DW. (2007) Cancer biomarker discovery in plasma using a tissue-targeted proteomic approach. Cancer Epidemiol Biomarkers Prev 16: 1915-1917.

Zigrino P, Lëffek S, Mauch C. (2005) Tumor-stroma interactions: their role in the control of tumor cell invasion. Biochimie 87: 321-328.

* cited by examiner

SEQUENCE LISTING

```
<160> NUMBER OF SEQ ID NOS: 6

<210> SEQ ID NO 1
<211> LENGTH: 3147
<212> TYPE: DNA
<213> ORGANISM: Homo sapiens

<400> SEQUENCE: 1
gtcgcgccat tttgccgggg tttgaatgtg aggcggagcg gcggcaggag cggatagtgc      60
cagctacggt ccgcggctgg ggttccctcc tccgtttctg tatccccacg agatcctata     120
gcaatggaac tcagcgatgc aaatctgcaa acactaacag aatatttaaa gaaaacactt     180
gatcctgatc ctgccatccg acgtccagct gagaaatttc ttgaatctgt tgaaggaaat     240
cagaattatc cactgttgct tttgacatta ctggagaagt cccaggataa tgttatcaaa     300
gtatgtgctt cagtaacatt caaaaactat attaaaagga actggagaat tgttgaagat     360
gaaccaaaca aaatttgtga agccgatcga gtggccatta aagccaacat agtgcacttg     420
atgcttagca gcccagagca aattcagaag cagttaagtg atgcaattag cattattggc     480
agagaagatt ttccacagaa atggcctgac ttgctgacag aaatggtgaa tcgctttcag     540
agtggagatt tccatgttat taatggagtc ctccgtacag cacattcatt atttaaaaga     600
taccgtcatg aatttaagtc aaacgagtta tggactgaaa ttaagcttgt tctggatgcc     660
tttgctttgc ctttgactaa tcttttttaag gccactattg aactctgcag tacccatgca     720
aatgatgcct ctgccctgag gattctgttt tcttccctga tcctgatctc aaaattgttc     780
tatagtttaa actttcagga tctccctgaa ttttgggaag gtaatatgga aacttggatg     840
aataatttcc atactctctt aacattggat aataagcttt tacaaactga tgatgaagag     900
gaagccggct tattggagct cttaaaatcc cagatttgtg ataatgccgc actctatgca     960
caaaagtacg atgaagaatt ccagcgatac ctgcctcgtt ttgttacagc catctggaat    1020
ttactagtta caacgggtca agaggttaaa tatgatttgt tggtaagtaa tgcaattcaa    1080
tttctggctt cagtttgtga gagacctcat tataagaatc tatttgagga ccagaacacg    1140
ctgacaagta tctgtgaaaa ggttattgtg cctaacatgg aatttagagc tgctgatgaa    1200
gaagcatttg aagataattc tgaggagtac ataaggagag atttggaagg atctgatatt    1260
```

```
gatactagac gcagggctgc ttgtgatctg gtacgaggat tatgcaagtt ttttgaggga    1320
cctgtgacag gaatcttctc tggttatgtt aattccatgc tgcaggaata cgcaaaaaat    1380
ccatctgtca actggaaaca caaagatgca gccatctacc tagtgacatc tttggcatca    1440
aaagcccaaa cacagaagca tggaattaca caagcaaatg aacttgtaaa cctaactgag    1500
ttctttgtga atcacatcct ccctgattta aaatcagcta atgtgaatga atttcctgtc    1560
cttaaagctg acggtatcaa atatattatg atttttagaa atcaagtgcc aaaagaacat    1620
cttttagtct cgattcctct cttgattaat catcttcaag ctggaagtat tgttgttcat    1680
acttacgcag ctcatgctct tgaacggctc tttactatgc gagggcctaa caatgccact    1740
ctctttacag ctgcagaaat cgcaccgttt gttgagattc tgctaacaaa ccttttcaaa    1800
gctctcacac ttcctggctc ttcagaaaat gaatatatta tgaaagctat catgagaagt    1860
ttttctctcc tacaagaagc cataatcccc tacatcccta ctctcatcac tcagcttaca    1920
cagaagctat tagctgttag taagaaccca agcaaacctc actttaatca ctacatgttt    1980
gaagcaatat gtttatccat aagaataact tgcaaagcta accctgctgc tgttgtaaat    2040
tttgaggagg cttgtttttt ggtgtttact gaaatcttac aaaatgatgt gcaagaattt    2100
attccatacg tcttcaagt gatgtctttg cttctggaaa cacacaaaaa tgacatcccg    2160
tcttcctata tggccttatt tcctcatctc cttcagccag tgctttggga agaacagga    2220 aatattcctg ctctagtgag gcttcttcaa gcattcttag aacgcggttc aaacacaata    2280
gcaagtgctg cagctgacaa aattcctggg ttactaggtg tctttcagaa gctgattgca    2340
tccaaagcaa atgaccacca aggtttttat cttctaaaca gtataataga gcacatgcct    2400
cctgaatcag ttgaccaata taggaaacaa atcttcattc tgctattcca gagacttcag    2460
aattccaaaa caaccaagtt tatcaagagt ttttttagtct ttattaattt gtattgcata    2520
aaatatgggg cactagcact acaagaaata tttgatggta tacaaccaaa atgtttggaa    2580
atggttttgg aaaaaattat tattcctgaa attcagaagg tatctggaaa tgtagagaaa    2640
aagatctgtg cggttggcat aaccaactta ctaacagaat gtcccccaat gatggacact    2700
gagtatacca aactgtggac tccattatta cagtctttga ttggtctttt tgagttaccc    2760
gaagatgata ccattcctga tgaggaacat tttattgaca tagaagatac accaggatat    2820
cagactgcct tctcacagtt ggcatttgct gggaaaaaag agcatgatcc tgtaggtcaa    2880
atggtgaata accccaaaat tcacctggca cagtcacttc acatgttgtc taccgcctgt    2940
ccaggaaggg ttccatcaat ggtgagcacc agcctgaatg cagaagcgct ccagtatctc    3000
caagggtacc ttcaggcagc cagtgtgaca ctgcttttaaa ctgcattttt ctaatgggct    3060
aaacccagat ggtttcctag gaatcacag gcttctgagc acagctgcat taaaacaaag    3120
gaagttttcc ttttgaactt gtcacga                                       3147
```

<210> SEQ ID NO 2
<211> LENGTH: 971
<212> TYPE: PRT
<213> ORGANISM: Homo sapiens

<400> SEQUENCE: 2

Met Glu Leu Ser Asp Ala Asn Leu Gln Thr Leu Thr Glu Tyr Leu Lys
1               5                   10                  15

Lys Thr Leu Asp Pro Asp Pro Ala Ile Arg Arg Pro Ala Glu Lys Phe
            20                  25                  30

Leu Glu Ser Val Glu Gly Asn Gln Asn Tyr Pro Leu Leu Leu Leu Thr
        35                  40                  45

```
Leu Leu Glu Lys Ser Gln Asp Asn Val Ile Lys Val Cys Ala Ser Val
    50                  55                  60

Thr Phe Lys Asn Tyr Ile Lys Arg Asn Trp Arg Ile Val Glu Asp Glu
65                  70                  75                  80

Pro Asn Lys Ile Cys Glu Ala Asp Arg Val Ala Ile Lys Ala Asn Ile
                85                  90                  95

Val His Leu Met Leu Ser Ser Pro Glu Gln Ile Gln Lys Gln Leu Ser
                100                 105                 110

Asp Ala Ile Ser Ile Ile Gly Arg Glu Asp Phe Pro Gln Lys Trp Pro
            115                 120                 125

Asp Leu Leu Thr Glu Met Val Asn Arg Phe Gln Ser Gly Asp Phe His
    130                 135                 140

Val Ile Asn Gly Val Leu Arg Thr Ala His Ser Leu Phe Lys Arg Tyr
145                 150                 155                 160

Arg His Glu Phe Lys Ser Asn Glu Leu Trp Thr Glu Ile Lys Leu Val
                165                 170                 175

Leu Asp Ala Phe Ala Leu Pro Leu Thr Asn Leu Phe Lys Ala Thr Ile
            180                 185                 190

Glu Leu Cys Ser Thr His Ala Asn Asp Ala Ser Ala Leu Arg Ile Leu
    195                 200                 205

Phe Ser Ser Leu Ile Leu Ile Ser Lys Leu Phe Tyr Ser Leu Asn Phe
210                 215                 220

Gln Asp Leu Pro Glu Phe Trp Glu Gly Asn Met Glu Thr Trp Met Asn
225                 230                 235                 240

Asn Phe His Thr Leu Leu Thr Leu Asp Asn Lys Leu Leu Gln Thr Asp
                245                 250                 255

Asp Glu Glu Glu Ala Gly Leu Leu Glu Leu Leu Lys Ser Gln Ile Cys
            260                 265                 270

Asp Asn Ala Ala Leu Tyr Ala Gln Lys Tyr Asp Glu Glu Phe Gln Arg
    275                 280                 285

Tyr Leu Pro Arg Phe Val Thr Ala Ile Trp Asn Leu Leu Val Thr Thr
290                 295                 300

Gly Gln Glu Val Lys Tyr Asp Leu Leu Val Ser Asn Ala Ile Gln Phe
305                 310                 315                 320

Leu Ala Ser Val Cys Glu Arg Pro His Tyr Lys Asn Leu Phe Glu Asp
                325                 330                 335

Gln Asn Thr Leu Thr Ser Ile Cys Glu Lys Val Ile Val Pro Asn Met
            340                 345                 350

Glu Phe Arg Ala Ala Asp Glu Glu Ala Phe Glu Asp Asn Ser Glu Glu
    355                 360                 365

Tyr Ile Arg Arg Asp Leu Glu Gly Ser Asp Ile Asp Thr Arg Arg Arg
370                 375                 380

Ala Ala Cys Asp Leu Val Arg Gly Leu Cys Lys Phe Phe Glu Gly Pro
385                 390                 395                 400

Val Thr Gly Ile Phe Ser Gly Tyr Val Asn Ser Met Leu Gln Glu Tyr
                405                 410                 415

Ala Lys Asn Pro Ser Val Asn Trp Lys His Lys Asp Ala Ala Ile Tyr
            420                 425                 430

Leu Val Thr Ser Leu Ala Ser Lys Ala Gln Thr Gln Lys His Gly Ile
    435                 440                 445

Thr Gln Ala Asn Glu Leu Val Asn Leu Thr Glu Phe Phe Val Asn His
450                 455                 460

Ile Leu Pro Asp Leu Lys Ser Ala Asn Val Asn Glu Phe Pro Val Leu
```

-continued

```
                465                 470                 475                 480
Lys Ala Asp Gly Ile Lys Tyr Ile Met Ile Phe Arg Asn Gln Val Pro
                485                 490                 495
Lys Glu His Leu Leu Val Ser Ile Pro Leu Leu Ile Asn His Leu Gln
                500                 505                 510
Ala Gly Ser Ile Val Val His Thr Tyr Ala Ala His Ala Leu Glu Arg
                515                 520                 525
Leu Phe Thr Met Arg Gly Pro Asn Asn Ala Thr Leu Phe Thr Ala Ala
530                 535                 540
Glu Ile Ala Pro Phe Val Glu Ile Leu Leu Thr Asn Leu Phe Lys Ala
545                 550                 555                 560
Leu Thr Leu Pro Gly Ser Ser Glu Asn Glu Tyr Ile Met Lys Ala Ile
                565                 570                 575
Met Arg Ser Phe Ser Leu Leu Gln Glu Ala Ile Ile Pro Tyr Ile Pro
                580                 585                 590
Thr Leu Ile Thr Gln Leu Thr Gln Lys Leu Leu Ala Val Ser Lys Asn
                595                 600                 605
Pro Ser Lys Pro His Phe Asn His Tyr Met Phe Glu Ala Ile Cys Leu
                610                 615                 620
Ser Ile Arg Ile Thr Cys Lys Ala Asn Pro Ala Ala Val Val Asn Phe
625                 630                 635                 640
Glu Glu Ala Leu Phe Leu Val Phe Thr Glu Ile Leu Gln Asn Asp Val
                645                 650                 655
Gln Glu Phe Ile Pro Tyr Val Phe Gln Val Met Ser Leu Leu Leu Glu
                660                 665                 670
Thr His Lys Asn Asp Ile Pro Ser Ser Tyr Met Ala Leu Phe Pro His
                675                 680                 685
Leu Leu Gln Pro Val Leu Trp Glu Arg Thr Gly Asn Ile Pro Ala Leu
                690                 695                 700
Val Arg Leu Leu Gln Ala Phe Leu Glu Arg Gly Ser Asn Thr Ile Ala
705                 710                 715                 720
Ser Ala Ala Ala Asp Lys Ile Pro Gly Leu Leu Gly Val Phe Gln Lys
                725                 730                 735
Leu Ile Ala Ser Lys Ala Asn Asp His Gln Gly Phe Tyr Leu Leu Asn
                740                 745                 750
Ser Ile Ile Glu His Met Pro Pro Glu Ser Val Asp Gln Tyr Arg Lys
                755                 760                 765
Gln Ile Phe Ile Leu Leu Phe Gln Arg Leu Gln Asn Ser Lys Thr Thr
                770                 775                 780
Lys Phe Ile Lys Ser Phe Leu Val Phe Ile Asn Leu Tyr Cys Ile Lys
785                 790                 795                 800
Tyr Gly Ala Leu Ala Leu Gln Glu Ile Phe Asp Gly Ile Gln Pro Lys
                805                 810                 815
Met Phe Gly Met Val Leu Glu Lys Ile Ile Pro Glu Ile Gln Lys
                820                 825                 830
Val Ser Gly Asn Val Glu Lys Lys Ile Cys Ala Val Gly Ile Thr Asn
                835                 840                 845
Leu Leu Thr Glu Cys Pro Pro Met Met Asp Thr Glu Tyr Thr Lys Leu
                850                 855                 860
Trp Thr Pro Leu Leu Gln Ser Leu Ile Gly Leu Phe Glu Leu Pro Glu
865                 870                 875                 880
Asp Asp Thr Ile Pro Asp Glu Glu His Phe Ile Asp Ile Glu Asp Thr
                885                 890                 895
```

```
Pro Gly Tyr Gln Thr Ala Phe Ser Gln Leu Ala Phe Ala Gly Lys Lys
            900                 905                 910

Glu His Asp Pro Val Gly Gln Met Val Asn Asn Pro Lys Ile His Leu
            915                 920                 925

Ala Gln Ser Leu His Met Leu Ser Thr Ala Cys Pro Gly Arg Val Pro
            930                 935                 940

Ser Met Val Ser Thr Ser Leu Asn Ala Glu Ala Leu Gln Tyr Leu Gln
945                 950                 955                 960

Gly Tyr Leu Gln Ala Ala Ser Val Thr Leu Leu
                965                 970

<210> SEQ ID NO 3
<211> LENGTH: 24
<212> TYPE: DNA
<213> ORGANISM: Homo sapiens

<400> SEQUENCE: 3
tatagcaatg gaactcagcg atgc                                          24

<210> SEQ ID NO 4
<211> LENGTH: 24
<212> TYPE: DNA
<213> ORGANISM: Homo sapiens

<400> SEQUENCE: 4
agtttaaagc agtgtcacac tggc                                          24

<210> SEQ ID NO 5
<211> LENGTH: 30
<212> TYPE: DNA
<213> ORGANISM: Homo sapiens

<400> SEQUENCE: 5
ggatccatgg aactcagcga tgcaaatctg                                    30

<210> SEQ ID NO 6
<211> LENGTH: 29
<212> TYPE: DNA
<213> ORGANISM: Homo sapiens

<400> SEQUENCE: 6
ctcgagttaa agcagtgtca cactggctg                                     29
```

METHODS AND KITS FOR DETECTION OF CANCER METASTASIS

FIELD OF THE INVENTION

The invention provides the method and kit for diagnosing cancer metastasis. In particular, the invention provides the method and kit for measuring the level of the cellular apoptosis susceptibility (CAS) protein (GenBank accession no. U33286) or CAS polypeptide in the body fluids from a mammal to screen or diagnose the metastasis of cancers.

BACKGROUND OF THE INVENTION

Recently, cancer treatment has seen notable progress. Especially, the success rate of cure of a primary cancer by surgery or radiotherapy has been improved, thereby contributing greatly to the progress in cancer treatment. Screening of metastatic cancers is important in cancer treatment. Non-metastatic cancers are usually respectable, while metastatic cancers are usually unrespectable. The non-metastatic tumors are usually treated by surgical elimination. For patients with cancer that has spread or metastasised, radiation, chemotherapy, or a combination of chemotherapy and radiation will be offered as treatment. Therefore, method and kit that can diagnosis whether a cancer is metastatic would be helpful for determining the most effective way to treat the cancer. Serological cancer metastatic markers are useful for screening, determining diagnoses and prognoses, assessing responses to therapy, and monitoring for cancer recurrence, and thus are highly beneficial in diagnosing and treating cancers (Basuyau et al., 2001; Thomas and Sweep, 2001; Petricoin et al., 2006; Brenner et al., 2007; Rodrigues et al., 2007; Shields et al., 2007; Skates et al., 2007; Wang et al., 2007; Zhang and Chan, 2007).

Metastasis of cancer involves a multi-step process, including the ability of cancer cells to escape from their original position, degrade the extracellular matrix (ECM), and migrate through ECM (Bogenrieder and Herlyn, 2003). Currently, the mechanism of cancer metastasis is presumed to be as follows. (1) Cancer cells proliferate in a primary cancer colony; (2) new blood vessels are newly formed; (3) the malignant cancer cells infiltrate and penetrate the newly formed blood vessels; (4) the cancer cells circulate within the human body; (5) the cancer cells reach a target organ; (6) the cancer cells extravasate from blood vessels; (7) the cancer cells proliferate in the target organ; and (8) a metastatic focus is formed.

Metastatic cancer cells can secrete extracellular matrix (ECM)-degradation protease to degrade ECM during metastasis. MMPs (matrix metalloproteinases) are enzymes involved in the degradation of ECM (Nguyen et al., 1998; Holmbeck et al., 2004; Lee et al., 2007). MMP-2 plays a major role in ECM degradation during cancer metastasis (Stetler-Stevenson et al., 1993). Experiment showed that MMPs production could be regulated at the level of secretion (Taraboletti et al., 2000). Thus, the metastatic cancer cells may develop strong secretory ability to enhance MMPs secretion and thereby enhancing their metastasis abilities (Moser et al., 1994; Jena, 2005).

The cellular apoptosis susceptibility (CAS, or CSE1L/CAS) protein (GenBank accession no. U33286) was identified in a study of an antisense DNA fragment that is capable of causing cell resistance to apoptosis induced by *Pseudomonas* exotoxin, diphtheria toxin, and tumor necrosis factors (Brinkmann et al., 1995a). CAS protein also regulates apoptosis induced by cypermethrin (Izaguirre et al., 2006), interferon-γ (Jiang et al., 2007), and chemotherapeutic drugs (Liao et al., 2008a; Liao et al., 2008b). The CAS gene is the human homologue of the yeast chromosome segregation gene, CSE1 (Brinkmann et al., 1995b). As CAS protein is able to associate with microtubules (Scherf et al., 1996) and importin-α, a nuclear-transport receptor (Kutay et al., 1997), CAS is mainly distributed in the nuclei and cytoplasm surrounding perinuclear areas of cells. Pathological studies showed that the expression of CAS protein was correlated positively with high cancer stage and high cancer grade as well as worse outcome of the cancer patients (Wellmann et al., 1997; Boni et al., 1999; Behrens et al., 2001; Peiro et al., 2001; Wellmann et al., 2001; Behrens et al., 2003; Seiden-Long et al., 2006).

U.S. Pat. No. 6,664,057 pertains to the identification of a novel amplicon on human chromosome 20q13.2 which is associated with cancer. U.S. Pat. No. 6,072,031 provides the cDNA and amino acid sequences for the cellular apoptosis susceptibility (CAS) protein are used to detect expression and amplification of the CAS gene in normal and cancer cells. An antisense CAS gene sequence introduced into living cells inhibits CAS protein activity and thus prevents or inhibits apoptosis in the cells. U.S. Pat. No. 5,759,782 provides the cDNA and amino acid sequences for the cellular apoptosis susceptibility (CAS) protein are used to detect expression and amplification of the CAS gene in normal and cancer cells. An antisense CAS gene sequence introduced into living cells inhibits CAS protein activity and thus prevents or inhibits apoptosis in the cells. U.S. Pat. No. 6,440,737 provides antisense compounds, compositions and methods for modulating the expression of CAS gene. U.S. Pat. No. 6,232,086 discloses the cDNA and amino acid sequences for a CAS protein that can be used to detect expression and amplification of the CAS gene in normal and cancer cells. U.S. Pat. No. 6,156,564 pertains to a method of detecting human proliferating cells comprising measuring a level of a human CAS protein in a human cell sample and detecting the human CAS protein at a level at least two times greater than the level of a human CAS protein in normal nonproliferating human cells. U.S. Pat. No. 6,207,380 provides polypeptides and polynucleotides useful for detecting, diagnosing, staging, monitoring, prognosticating, in vivo imaging, preventing or treating, or determining the predisposition of an individual to diseases and conditions of the urinary tract, such as urinary cancer, are described. These sequences are derived from keratin/cytokeratin, CAS, or mat-8 polypeptides and polynucleotides. U.S. Pat. No. 6,207,380 also provided are antibodies that specifically bind to keratin/cytokeratin, CAS, or mat-8-encoded polypeptides or proteins, which molecules are useful for the therapeutic treatment of urinary tract diseases, tumors or metastases. Thus, U.S. Pat. No. 6,207,380 describes using antibodies that specifically bind to keratin/cytokeratin, CAS, or mat-8 for the therapy of urinary tract diseases, tumors or metastases. The prior art above detect the expression of CAS gene in cell level. Therefore, according to the contents and claims described in these prior arts, non of these arts describe or claim measuring CAS level in the body fluids from a mammal for the screening or diagnosis of cancer metastasis.

Metastasis still remains the main cause of death for most cancer patients. Metastasis is the major characteristic of high-stage cancer and the major cause of cancer death. The obstacle to successful treatment of cancer continues to be the lack of sound markers that can screen metastatic cancers accurately. In colorectal cancers, they are one of the most common leading causes of cancer-related deaths in the world. Non-metastatic colorectal cancers are resectable, and the 5-year survival percentage can exceed 90%, whereas metastatic colorectal cancers are usually unresectable, and the 5-year survival percentage may be only about 5% (Breslow et al., 1997; Rex et al., 2006). Thus, a reliable serological marker would be helpful for screening metastatic colorectal cancers and would be beneficial for colorectal cancer treatment (Bresalier et al., 2004; Stein et al., 2006; Lassmann et al., 2007; Gupta et al., 2008; Ransohoff et al., 2008). The carcinoembryonic antigen (CEA), a heavily glycosylated protein associated with the progression of colorectal tumors, is the tumor marker most frequently used in assessing the prognosis of colorectal cancers (Gold and Freedman, 1965; Hammarström, 1999). By using a radio-immunoassay method, Thomson et al. reported that circulating CEA was positive in 97% of patients with colorectal cancer (Thomson et al. 1969). Nevertheless, the high blood CEA in bowel cancers apparently have a relevance with patients had advanced disease with extensive metastases, especially liver involvement (Moertel et al. 1993). Also, many studies have reported that elevation of CEA level in blood is not necessarily correlated well with the presence of metastasis of colon or rectal cancers (Hsu T C 2006; Saito et al., 2005); patients with benign colorectal diseases may also show raised serum CEA levels (Fong et al., 1985). Thus, the main clinical utility of CEA is in monitoring colorectal carcinoma after surgical resection, when increased values suggest recurrence and consistently normal values suggest the absence of recurrence (Go, 1976; Savrin et al., 1979; Chu et al., 1991). Therefore, there is still a need for more reliable cancer markers that can diagnose cancer metastasis more accurately, which in turn will be of great help to the diagnosis and prognosis of cancers as well as cancer treatment. Due to the difficulties in the current approaches to the diagnosis of cancer metastases, there is a need in the art for improved methods and kits for diagnosing cancer metastasis.

SUMMARY OF THE INVENTION

The invention provides a method of detecting the metastasis of cancers. The method comprising the steps of: (a) providing the body fluids from a mammal; and (b) measuring the level of CAS protein or CAS polypeptide in the body fluids to screen or diagnose the metastasis of cancers.

The invention also provides a kit for assaying CAS protein or CAS polypeptide in the body fluids from a mammal to detecting metastasis of cancers, which comprises CAS protein specific antibodies.

BRIEF DESCRIPTION OF THE INVENTION

FIG. 1 refers to vesicle-like staining of CAS protein in cytoplasmic areas near the cell membrane and cell protrusions of MCF-7 cells. The cellular distribution of CAS protein was analyzed by immunofluorescence with the clone 24 anti-CAS monoclonal antibody. Note the vesicle-like staining of CAS (arrows) in the cell protrusions of cells marked with X1 and X2. The scale bar represents 30 μm.

Figure 2:
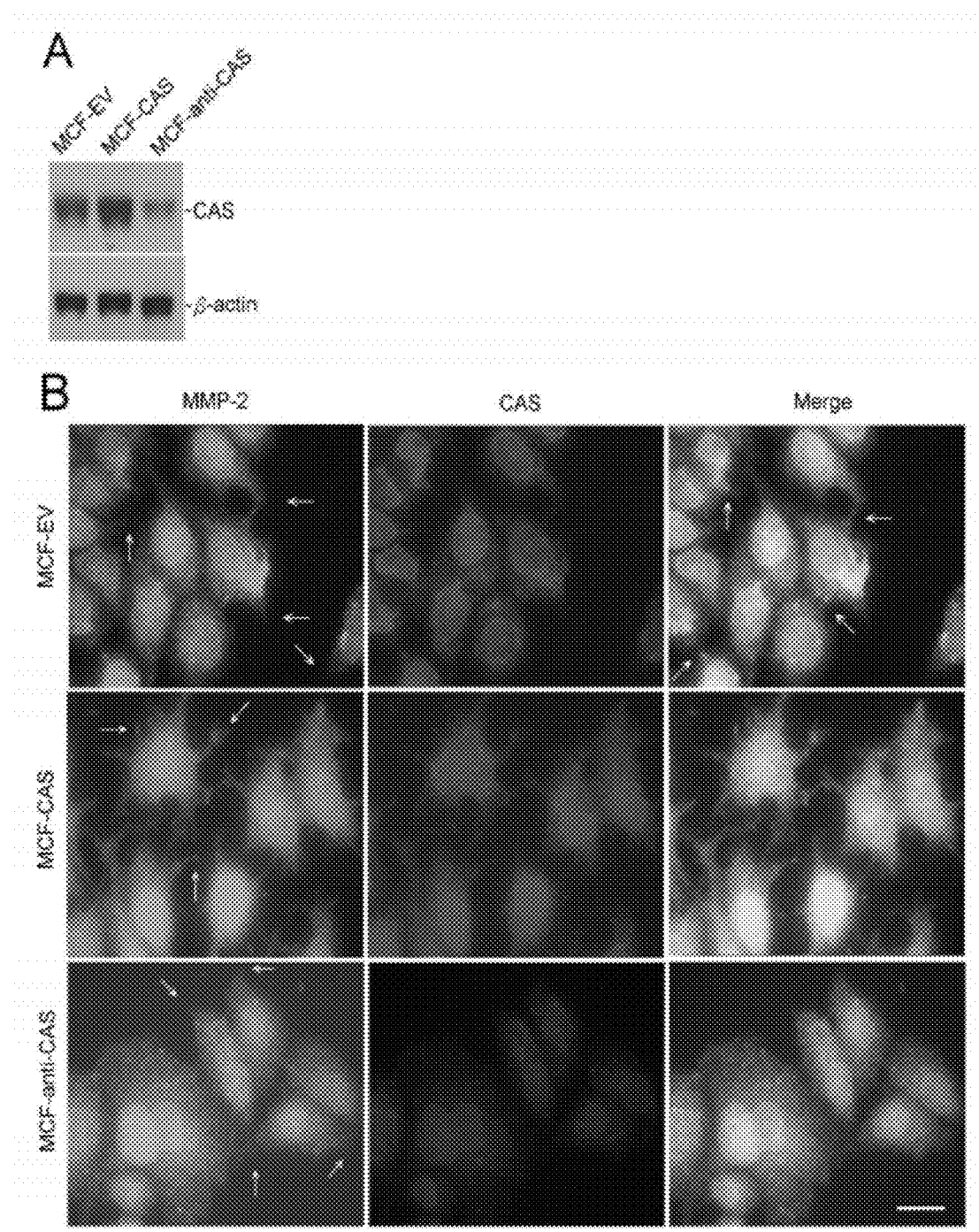

FIG. 2 refers to CAS expression regulates the distribution of MMP-2 in the tip or edge ends of the cell protrusions of MCF-7 cells analyzed by immunofluorescence with anti-CAS antibody and anti-MMP-2 antibody. (A) The expression of CAS in MCF-EV, MCF-CAS, and MCF-anti-CAS were analyzed by immunoblotting with anti-CAS antibody. (B) CAS expression regulates the distribution of MMP-2 in the tip or edge ends of the cell protrusions. Please note the increased distribution of CAS and MMP-2 in the tip or edge ends of the cell protrusions of MCF-CAS cells, and the decreased distribution of CAS and MMP-2 in the tip or edge ends of the cell protrusions of MCF-anti-CAS cells. The brightness and contrast of the fluorescence in the photo was strengthened to emphasize the colocalization of CAS with MMP-2-containing vesicle in the tip or edge ends of cell protrusions. Arrows indicate some of the cell protrusions of MCF-EV, MCF-CAS, and MCF-anti-CAS cells. The scale bar represents 20 μm.

Figure 3:
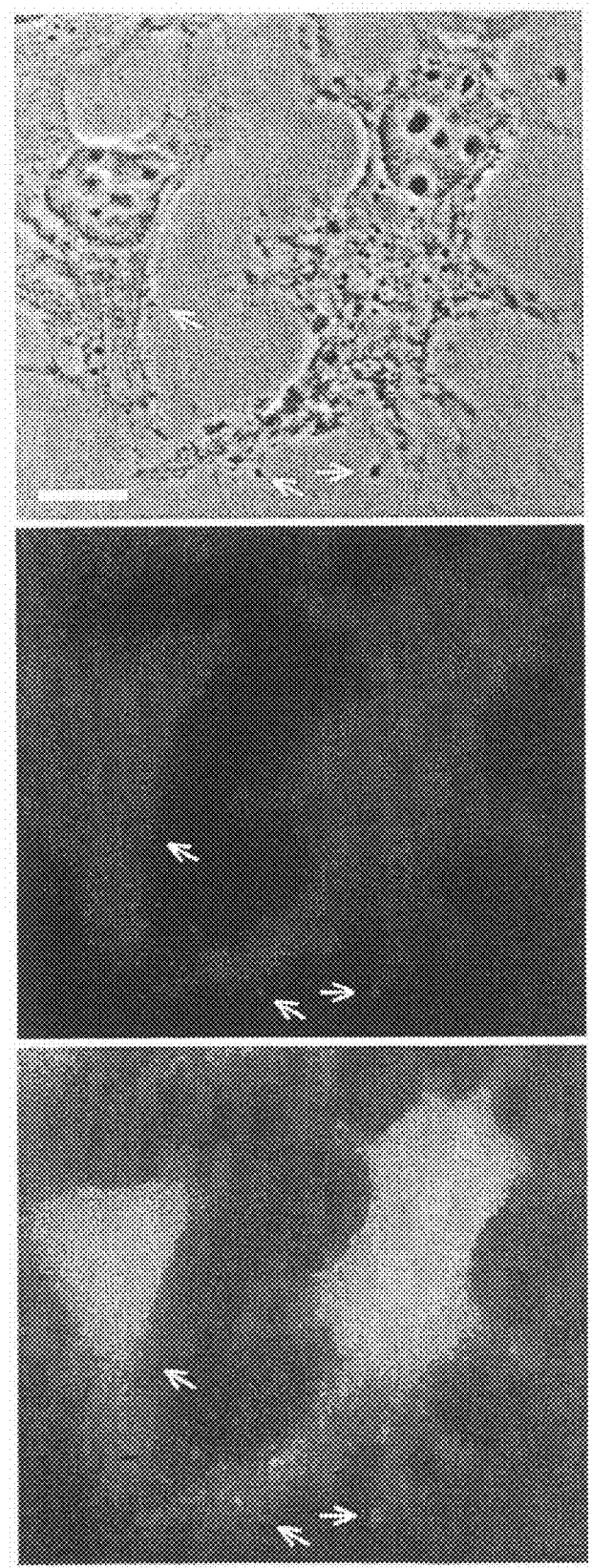

FIG. 3 refers to a high-resolution photograph showing colocalization of CAS with MMP-2 in vesicles surrounding the outside of cell membrane. Colocalizations of CAS with MMP-2 in MCF-CAS cells were analyzed by immunofluorescence with anti-CAS antibody and anti-MMP-2 antibody. Note the colocalization of CAS with MMP-2 in vesicles surrounding the outside of cell membrane (arrows). The brightness and contrast of the fluorescence in the photo was strengthened to emphasize the colocalization of CAS with MMP-2-containing vesicle surrounding the outsides of cell membrane. The scale bar represents 30 μm.

Figure 4:
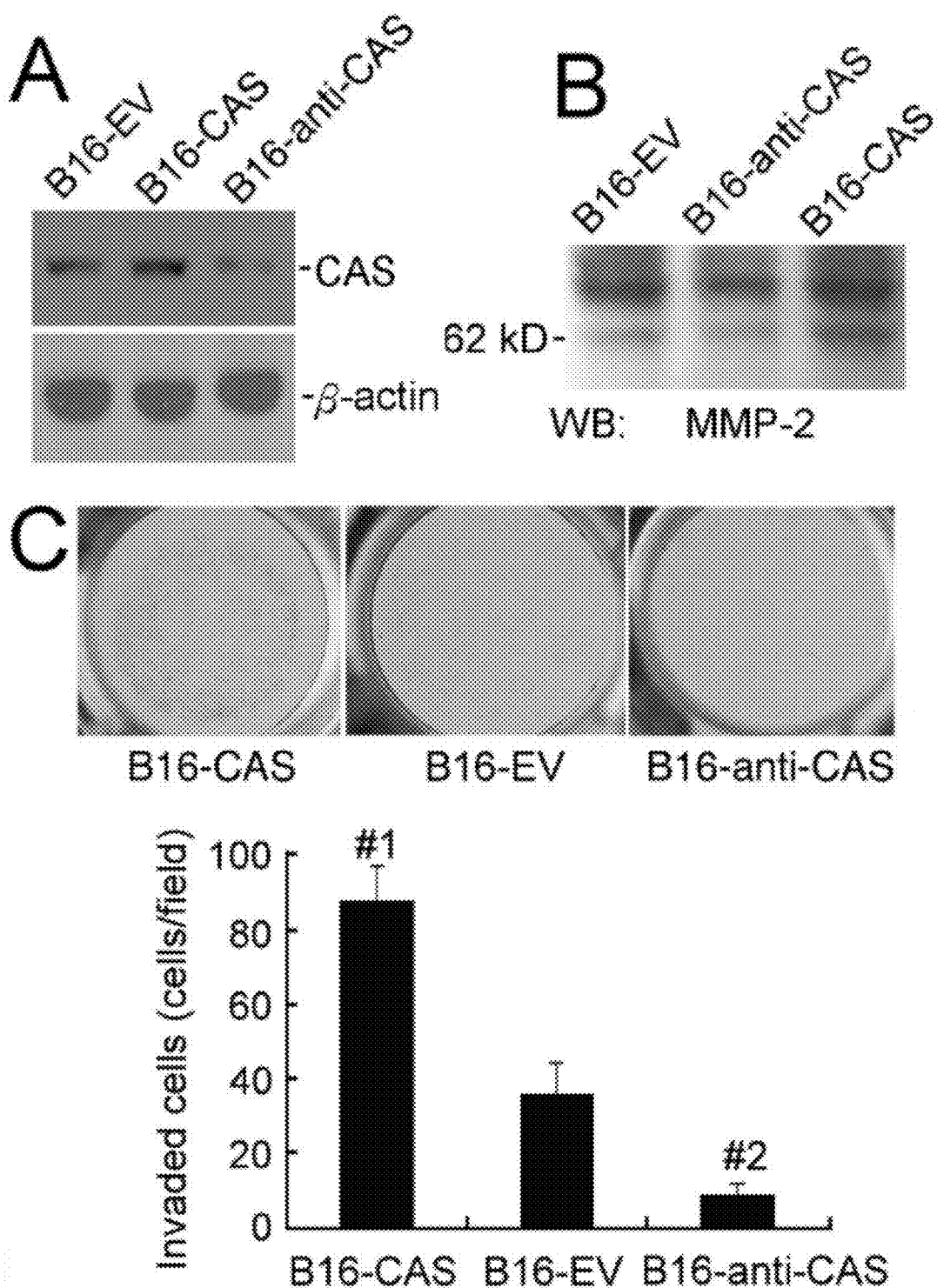

FIG. 4 refers to enhanced CAS expression increases the invasion of B16-F10 melanoma cells. (A) Analyses of CAS expression in B16-EV, B16-anti-CAS, and B16-CAS cells by immunoblotting with anti-CAS antibody. (B) Immunoblotting analyses of the conditioned media collected from B16-EV, B16-anti-CAS, and B16-CAS cells with anti-MMP-2 antibody. The immunoblotting assays were repeated three times and showed similar results; a representative immunoblot is shown here. (C) Matrigel-based invasion assays of B16-EV, B16-anti-CAS, and B16-CAS cells. The upper is a representative photograph of the invaded cells. Data are represented as the mean of three independent experiments. Increased CAS expression enhanced the invasion of B16-F10 cells by 249.2%, and reduced CAS expression inhibited the invasion of B16-F10 cells by 75.7%. #1 P=0.0019, compared to that of the B16-EV cells. #2 P=0.0073, compared to that of the B16-EV cells.

Figure 5:
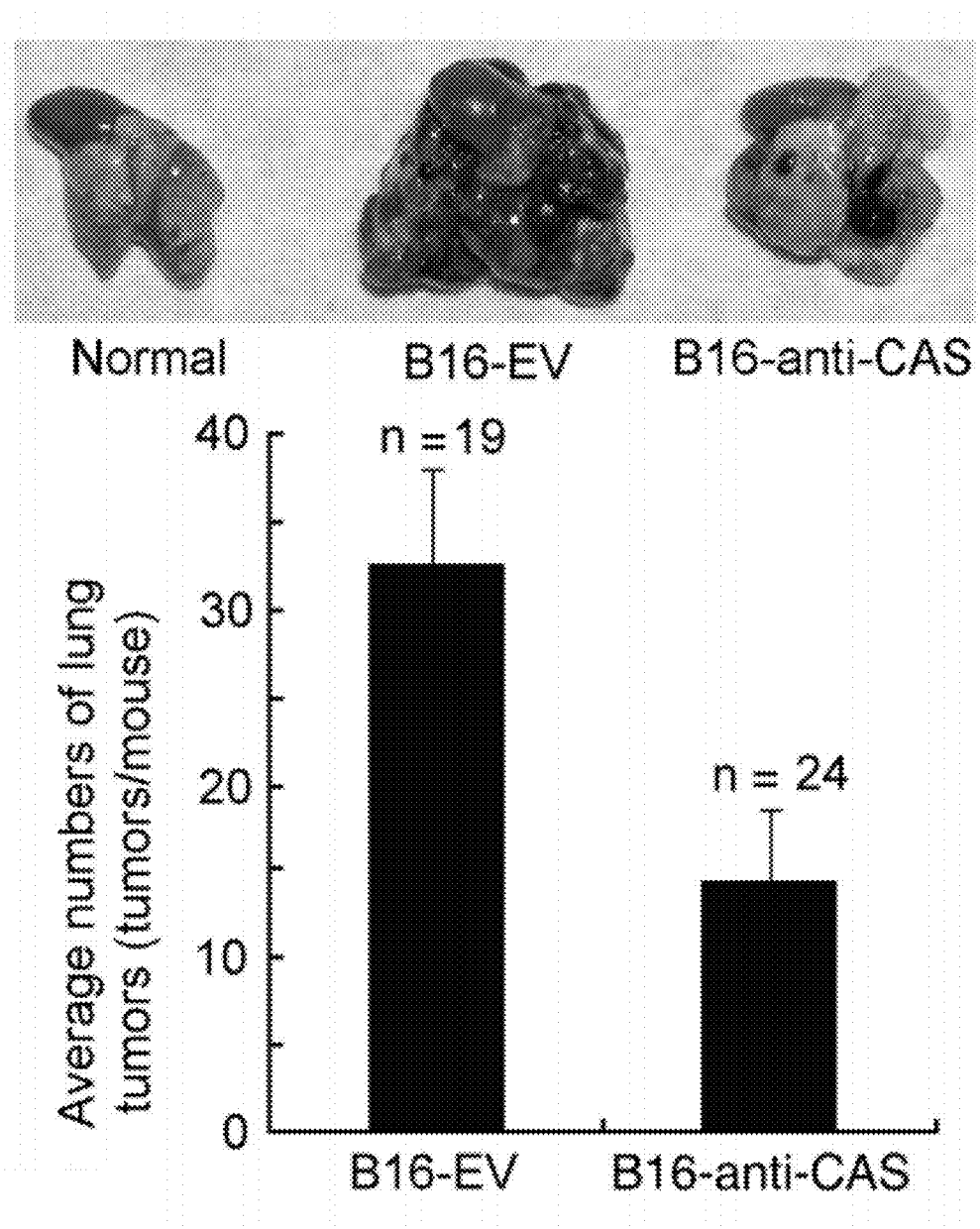

FIG. 5 refers to reduced CAS expression decreased the pulmonary metastasis of B16-F10 cells. The average lung tumor numbers of mice injected with B16-EV cells were 32.7±6.5 tumors/mouse (average tumor diameter 2.6±1.8 mm) and were 14.3±4.6 tumors/mouse (average tumor diameter 2.5±1.5 mm) for mice injected with B16-anti-CAS cells. Reduced CAS expression decreased the pulmonary metastasis of B16-F10 cells by 56% in C57BL/6 mice (P=0.0107). Eleven B16-EV cells-injected mice and six B16-anti-CAS cells-injected mice passed away three weeks after injection. Thus, anti-CAS transfection also reduces the mortality of mice injected with B16-F10 cells; probably due to anti-CAS transfection reduces the metastasis ability of B16-F10 cells. The results of animal tumor metastasis experiment indicate that CAS can regulate the metastasis of cancers.

Figure 6:
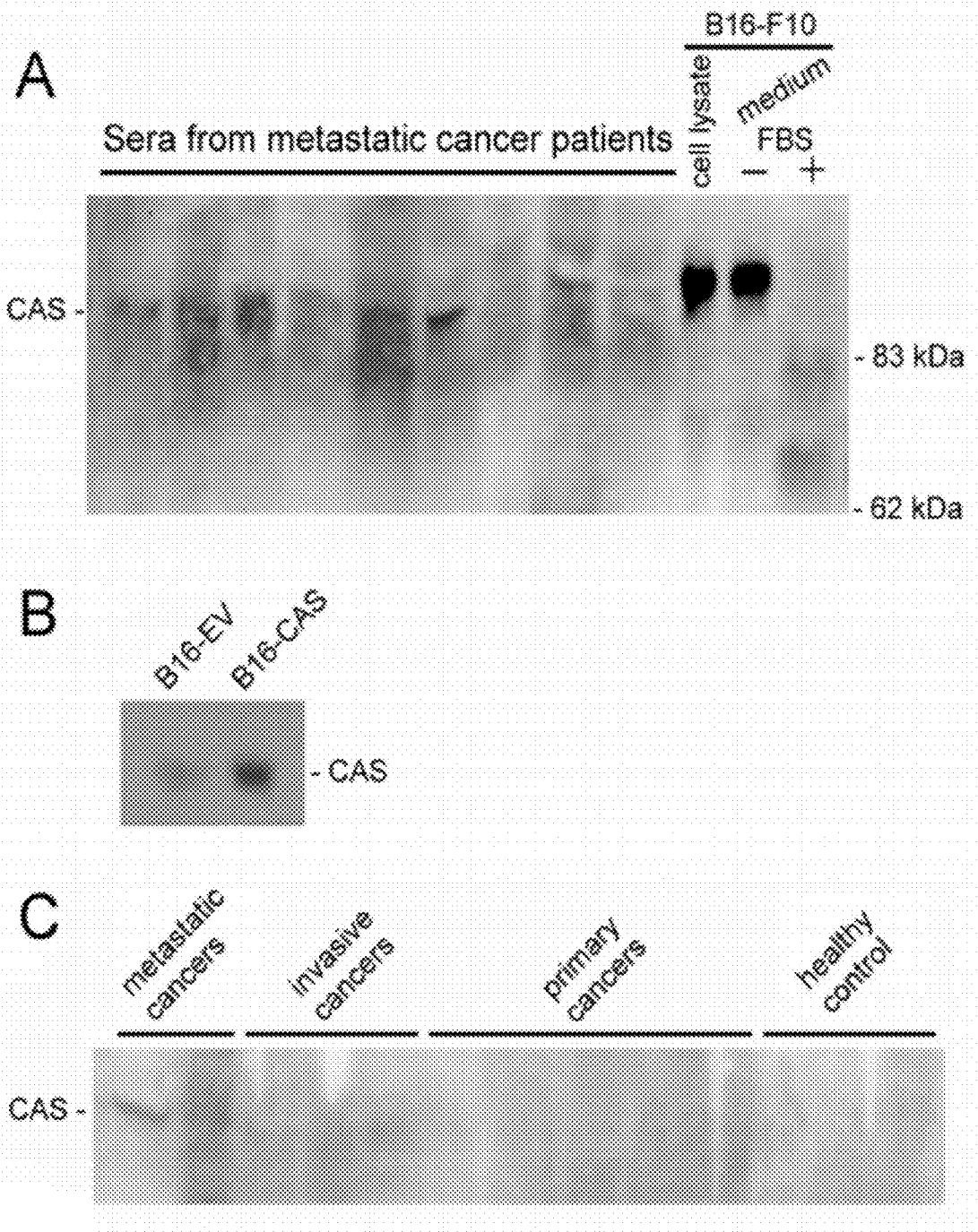

FIG. 6 shows that CAS is a secretory protein and presence of secretory CAS protein in sera of patients with metastatic cancer. (A) Immunoblotting analyses of serum samples collected from patients with metastatic cancer with the clone 24 anti-CAS antibody. Thirty microliters of each serum sample and 60 μl of each conditioned medium supplemented with or without FBS collected from B16-F10 cells were applied in the assay as indicated. A well loaded with the total cell lysate of B16-F10 cells was used for the control. Note that secretory CAS protein was detectable in sera of patients with metastatic cancer and in the conditioned medium of serum-starved B16-F10 cells. (B) Enhanced CAS expression increased the secretion of CAS protein in the medium. Conditioned media collected from serum-starved B16-EV and B16-CAS cells were subjected to immunoblotting with the anti-CAS antibody. (C) Immunoblotting analyses of CAS levels in sera collected from healthy donors and patients with metastatic, invasive, or primary cancers with the anti-CAS antibody. Each immunoblotting assay was repeated three times and showed similar results; representative immunoblots are shown here.

Figure 7:
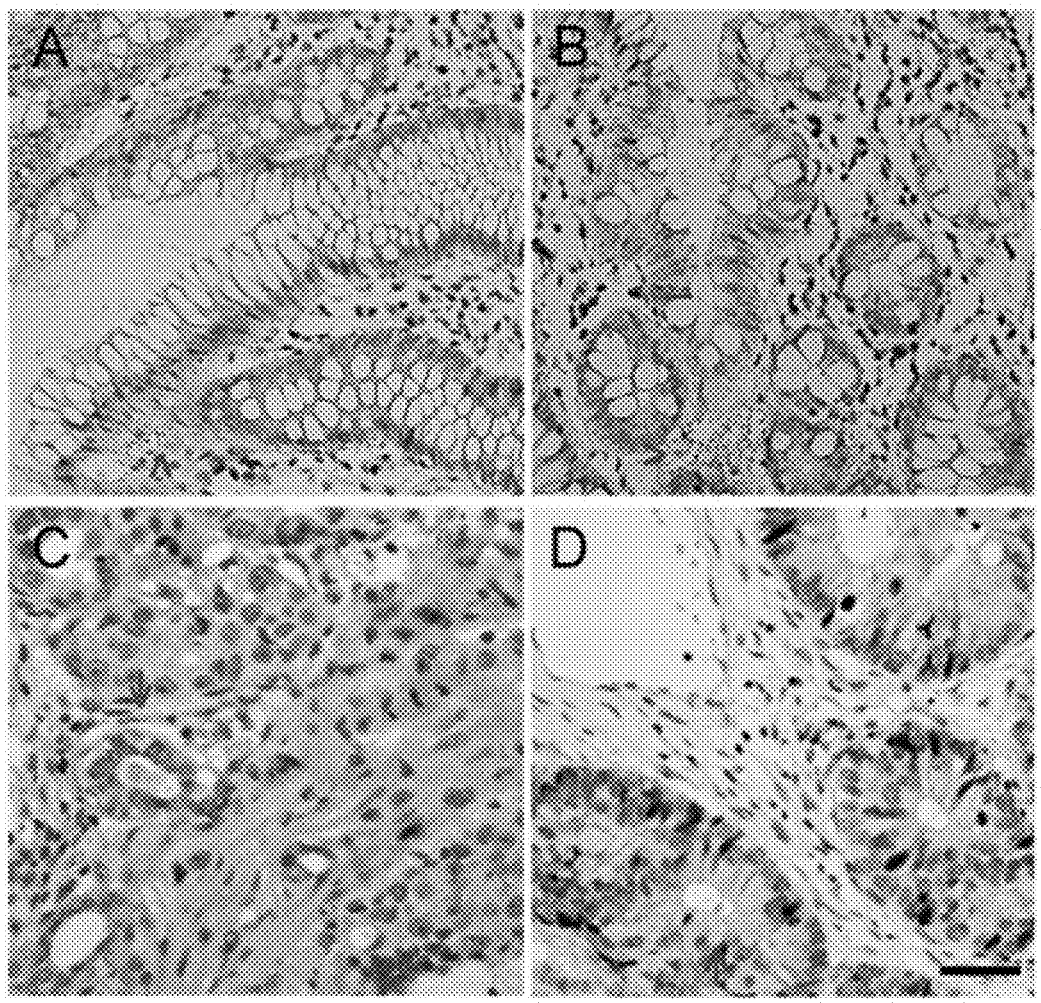

FIG. 7 shows that CAS is positively stained in the stroma and gland lumen of metastatic cancer tissues. Distributions of CAS in the metastatic colorectal (A, B, and D) and breast (C) cancer tissues were analyzed by immunohistochemistry with the clone 24 anti-CAS monoclonal antibody. Note the positive staining of CAS in the stroma (A and B, arrowheads), ductal lumen (C, arrows), and gland lumen (D, arrows) of cancer tissues. The scale bar represents 50 µm.

Figure 8:
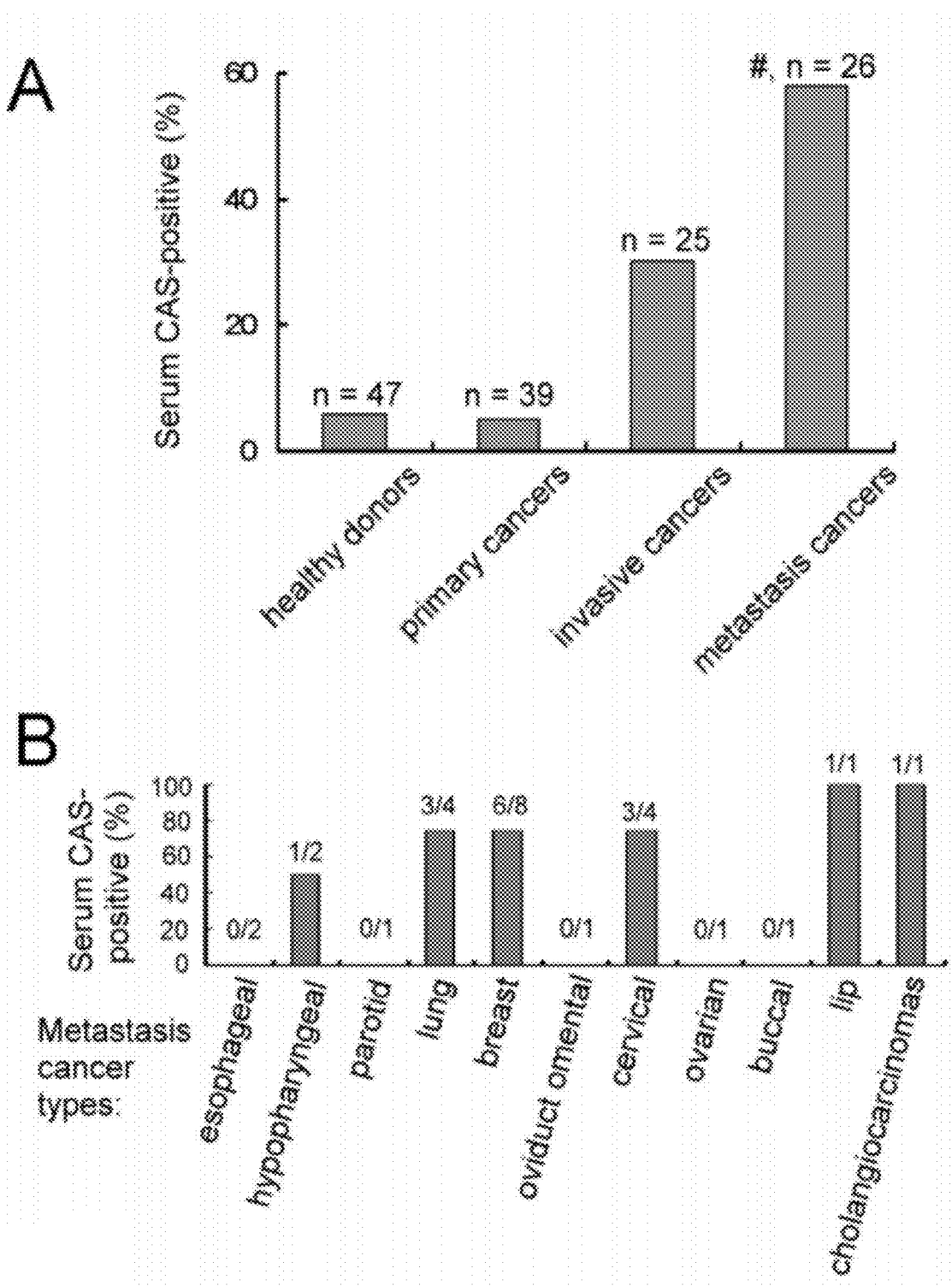

FIG. 8 shows a higher prevalence of secretory CAS in sera of patients with metastatic cancer. (A) The prevalence of serum CAS in healthy donors and patients with primary, invasive, and metastasis cancers were determined by ELISA. # Significant difference between the metastatic cancer group and primary cancer group (P<0.01). (B) Metastatic cancer types and the ratio of serum CAS detected in the metastatic cancers. The numbers of serum CAS-positive cases of each cancer type to the total numbers of each metastasis cancer type are indicated.

Figure 9:
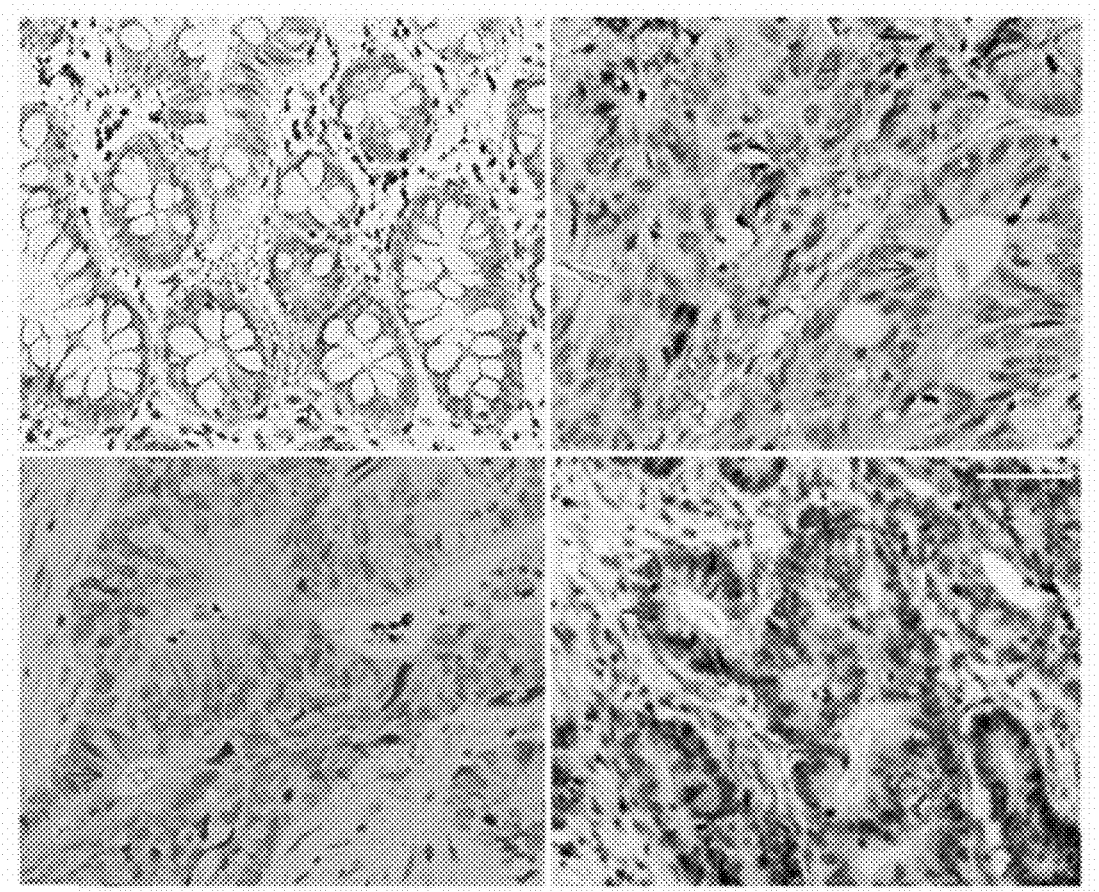

FIG. 9 shows positive staining of CAS in the gland lumen of metastatic colorectal cancer tissues. The distributions of CAS in metastatic colorectal cancer tissues were analyzed by immunohistochemistry with the clone 24 anti-CAS monoclonal antibody. Note the positive staining of CAS in the stroma (arrowheads) and the gland lumen (arrows) of metastatic colorectal cancer tissues. The scale bar represents 50 µm.

Figure 10:
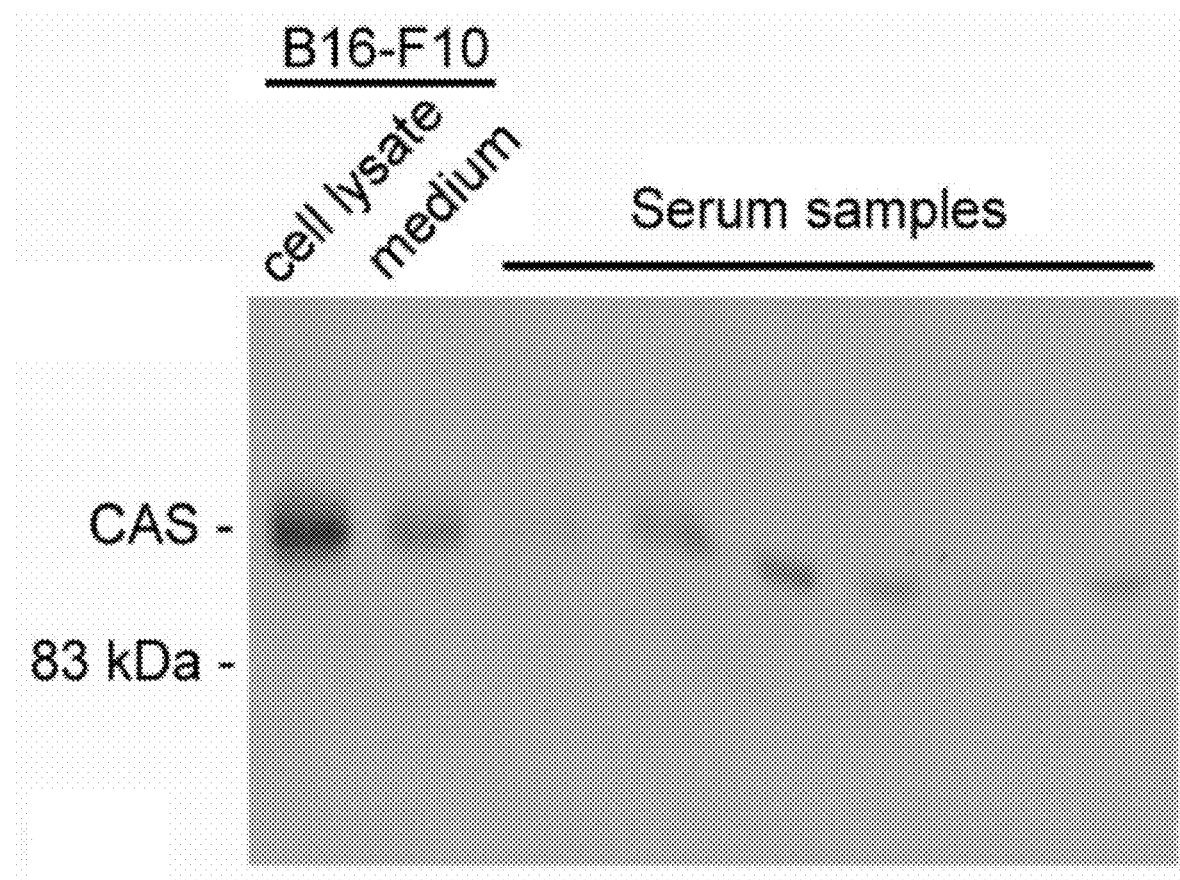

FIG. 10 shows CAS protein is present in sera of patients with metastatic colorectal cancer. Immunoblotting analyses of conditioned medium harvested from serum-starved B16-F10 cells and serum samples collected from metastatic colorectal cancer patients with the clone 24 anti-CAS monoclonal antibody. A well loaded with the total cell lysate of B16-F10 cells was used as the control. Note that secretory CAS protein was detectable in the sera of patients with metastasis colorectal cancer and the conditioned medium of serum-starved B16-F10 cells. The immunoblotting assay was repeated three times and showed similar results; a representative immunoblot is shown here.

DETAILED DESCRIPTION

The present invention is the first to discover that CAS is a secretory protein associated with cancer metastasis and thus may have clinical utility in metastatic cancer screening and diagnosis.

"Metastasis" refers to the ability of cancer cells to disseminate and form new foci of growth at noncontiguous sites (i.e., to form metastases). The transition from in situ tumor growth to metastatic disease is defined by the ability of tumor cells of the primary site to invade local tissues and to cross tissue barriers. To initiate the metastatic process, carcinoma cells must first penetrate the epithelial basement membrane and then invade the interstitial stroma. For distant metastases, intravasation requires tumor cell invasion of the subendothelial basement membrane that must also be negotiated during tumor cell extravasation. The development of malignancy is also associated with tumor-induced angiogenesis, which not only allows expansion of the primary tumor, but also permits easy access to the vascular compartment due to defects in the basement membranes of newly formed blood vessels.

A "cancer" in an animal refers to the presence of cells possessing characteristics typical of cancer-causing cells, such as uncontrolled proliferation, immortality, metastatic potential, rapid growth and proliferation rate, and certain characteristic morphological features and cellular markers. In some circumstances, cancer cells are in the form of a tumor, but they may also exist alone within an animal, or circulate in the blood stream as independent cells, such as leukemic cells.

The phrase "detecting a cancer metastasis" or "diagnosing a cancer metastasis" refers to determining the presence or absence of cancer metastasis in a mammal. "Detecting a cancer metastasis" can also refer to obtaining indirect evidence regarding the likelihood of the presence of metastasis of cancerous cells in the mammal. Detecting a cancer can be accomplished using the methods of this invention alone, in combination with other methods, or in light of other information regarding the state of health of the mammal.

"body fluids" means fluids that are excreted or secreted from the body as well as fluids which normally are not excreted or secreted from the body, such as serum, urine, ascites, pleural effusion, saliva or stool. One skilled in the art understands that body fluid samples can be diluted, if desired, prior to analysis. "Providing the body fluids" means to obtain the body fluids for use in the methods described in this invention.

A method of detecting metastasis of cancers in the body fluids from a mammal, the method comprising the steps of: (a) providing the body fluids from the mammal; and (b) the measurement of CAS protein level or CAS polypeptide in the body fluids to screen or diagnose the metastasis of cancers.

The CAS protein and its gene are known in the art. The DNA sequences of CAS gene (GenBank accession no. U33286) are shown below:

SEQ ID NO:1

```
  1 gtcgcgccat tttgccgggg tttgaatgtg aggcggagcg gcggcaggag cggatagtgc 61 cagctacggt ccgcggctgg ggttccctcc tccgtttctg tatccccacg agatcctata 121 gcaatggaac tcagcgatgc aaatctgcaa acactaacag aatatttaaa gaaaacactt 181 gatcctgatc ctgccatccg acgtccagct gagaaatttc ttgaatctgt tgaaggaaat 241 cagaattatc cactgttgct tttgacatta ctgagaagt cccaggataa tgttatcaaa 301 gtatgtgctt cagtaacatt caaaaactat attaaaagga actggagaat tgttgaagat 361 gaaccaaaca aaatttgtga agccgatcga gtggccatta aagccaacat agtgcacttg 421 atgcttagca gcccagagca aattcagaag cagttaagtg atgcaattag cattattggc 481 agagaagatt tccacagaa atggcctgac ttgctgacag aaatggtgaa tcgctttcag 541 agtggagatt ccatgttat taatggagtc ctccgtacag cacattcatt atttaaaaga
```

-continued

```
 601 taccgtcatg aatttaagtc aaacgagtta tggactgaaa ttaagcttgt tctggatgcc
 661 tttgctttgc ctttgactaa tcttttaag gccactattg aactctgcag tacccatgca
 721 aatgatgcct ctgccctgag gattctgttt tcttccctga tcctgatctc aaaattgttc
 781 tatagtttaa actttcagga tctccctgaa ttttgggaag gtaatatgga aacttggatg
 841 aataatttcc atactctctt aacattggat aataagcttt tacaaactga tgatgaagag
 901 gaagccggct tattggagct cttaaaatcc cagatttgtg ataatgccgc actctatgca
 961 caaaagtacg atgaagaatt ccagcgatac ctgcctcgtt ttgttacagc catctggaat
1021 ttactagtta caacgggtca agaggttaaa tatgattttgt tggtaagtaa tgcaattcaa
1081 tttctggctt cagtttgtga gagacctcat tataagaatc tatttgagga ccagaacacg
1141 ctgacaagta tctgtgaaaa ggttattgtg cctaacatgg aatttagagc tgctgatgaa
1201 gaagcatttg aagataattc tgaggagtac ataaggagag atttggaagg atctgatatt
1261 gatactagac gcagggctgc ttgtgatctg gtacgaggat tatgcaagtt ttttgaggga
1321 cctgtgacag gaatcttctc tggttatgtt aattccatgc tgcaggaata cgcaaaaaat
1381 ccatctgtca actggaaaca caaagatgca gccatctacc tagtgacatc tttggcatca
1441 aaagcccaaa cacagaagca tggaattaca caagcaaatg aacttgtaaa cctaactgag
1501 ttctttgtga atcacatcct ccctgattta aaatcagcta atgtgaatga atttcctgtc
1561 cttaaagctg acggtatcaa atatattatg atttttagaa atcaagtgcc aaaagaacat
1621 cttttagtct cgattcctct cttgattaat catcttcaag ctggaagtat tgttgttcat
1681 acttacgcag ctcatgctct tgaacggctc tttactatgc gagggcctaa caatgccact
1741 ctctttacag ctgcagaaat cgcaccgttt gttgagattc tgctaacaaa ccttttcaaa
1801 gctctcacac ttcctggctc ttcagaaaat gaatatatta tgaaagctat catgagaagt
1861 ttttctctcc tacaagaagc cataatcccc tacatcccta ctctcatcac tcagcttaca
1921 cagaagctat tagctgttag taagaaccca agcaaacctc actttaatca ctacatgttt
1981 gaagcaatat gtttatccat aagaataact tgcaaagcta accctgctgc tgttgtaaat
2041 tttgaggagg ctttgttttt ggtgtttact gaaatcttac aaaatgatgt gcaagaattt
2101 attccatacg tcttccaagt gatgtctttg cttctggaaa cacacaaaaa tgacatcccg
2161 tcttcctata tggccttatt tcctcatctc cttcagccag tgctttggga agaacagga
2221 aatattcctg ctctagtgag gcttcttcaa gcattcttag aacgcggttc aaacacaata
2281 gcaagtgctg cagctgacaa aattcctggg ttactaggtg tctttcagaa gctgattgca
2341 tccaaagcaa atgaccacca aggttttat cttctaaaca gtataatga gcacatgcct
2401 cctgaatcag ttgaccaata taggaaacaa atcttcattc tgctattcca gagacttcag
2461 aattccaaaa caaccaagtt tatcaagagt ttttagtct ttattaattt gtattgcata
2521 aaatatgggg cactagcact acaagaaata tttgatggta tacaaccaaa aatgtttgga
2581 atggttttgg aaaaaattat tattcctgaa attcagaagg tatctggaaa tgtagagaaa
2641 aagatctgtg cggttggcat aaccaactta ctaacagaat gtcccccaat gatggacact
2701 gagtatacca aactgtggac tccattatta cagtctttga ttggtctttt tgagttaccc
2761 gaagatgata ccattcctga tgaggaacat tttattgaca tagaagatac accaggatat
2821 cagactgcct tctcacagtt ggcatttgct gggaaaaaag agcatgatcc tgtaggtcaa
2881 atggtgaata accccaaaat tcacctggca cagtcacttc acatgttgtc taccgcctgt
2941 ccaggaaggg ttccatcaat ggtgagcacc agcctgaatg cagaagcgct ccagtatctc
3001 caagggtacc ttcaggcagc cagtgtgaca ctgctttaaa ctgcatttt ctaatgggct
```

3061 aaacccagat ggtttcctag gaaatcacag gcttctgagc acagctgcat taaaacaaag 3121 gaagttttcc ttttgaactt gtcacga The amino acid sequences of the CAS protein (Protein ID Accession No. AAC50367.1) are shown below:

SEQ ID NO:2
MELSDANLQTLTEYLKKTLDPDPAIRRPAEKFLESVEGNQNYPLLLLTLL

EKSQDNVIKVCASVTFKNYIKRNWRIVEDEPNKICEADRVAIKANIVHLM

LSSPEQIQKQLSDAISIIGREDFPQKWPDLLTEMVNRFQSGDFHVTNGVL

RTAHSLFKRYRHEFKSNELWTEIKLVLDAFALPLTNLFKATIELCSTHAN

DASALRILFSSLILISKLFYSLNFQDLPEFWEGNMETWMNNFHTLLTLDN

KLLQTDDEEEAGLLELLKSQICDNAALYAQKYDEEFQRYLPRFVTAIWNL

LVTTGQEVKYDLLVSNAIQFLASVCERPHYKNLFEDQNTLTSICEKVIVP

NMEFRAADEEAFEDNSEEYIRRDLEGSDIDTRRRAACDLVRGLCKFFEGP

VTGIFSGYVNSMLQEYAKNPSVNWKHKDAAIYLVTSLASKAQTQKHGITQ

ANELVNLTEFFVNHILPDLKSANVNEFPVLKADGIKYIMIFRNQVPKEHL

LVSIPLLINHLQAGSIVVHTYAAHALERLFTMRGPNNATLFTAAEIAPFV

EILLTNLFKALTLPGSSENEYIMKAIMRSFSLLQEAIIPYIPTLITQLTQ

KLLAVSKNPSKPHFNHYMFEAICLSIRITCKANPAAVVNFEEALFLVFTE

ILQNDVQEFIPYVFQVMSLLLETHKNDIPSSYMALFPHLLQPVLWERTGN

IPALVRLLQAFLERGSNTIASAAADKIPGLLGVFQKLIASKANDHQGFYL

LNSIIEHMPPESVDQYRKQIFILLFQRLQNSKTTKFIKSFLVFTNLYCIK

YGALALQEIFDGIQPKMFGMVLEKIIIPEIQKVSGNVEKKICAVGITNLL

TECPPMMDTEYTKLWTPLLQSLIGLFELPEDDTIPDEEHFIDIEDTPGYQ

TAFSQLAFAGKKEHDPVGQMVNNPKIHLAQSLHMLSTACPGRVPSMVSTS

LNAEALQYLQGYLQAASVTLL

According to one embodiment of the invention, the mammal is a human. According to embodiments of the invention, the measurement of the CAS protein level can be achieved by detecting the CAS protein or CAS polypeptide level in the body fluids using immunological binding assays.

Detection is based on measuring the level of CAS protein or CAS polypeptide in body fluids. The CAS protein can be detected and/or quantified using any of a number of well-known immunological binding assays. Immunoassays typically use direct or indirect labeling agents to label the complex formed by the antibody and antigen. The labeling agent can itself be one of the moieties comprising the antibody/antigen complex, i.e., a direct labeling agent. Thus, the labeling agent may be a labeled CAS protein or a labeled anti-CAS antibody. Alternatively, the labeling agent can be a third moiety, such as a secondary antibody, that specifically binds to the antibody/CAS protein complex (a secondary antibody is typically specific to antibodies of the species from which the first antibody is derived). The labeling agent can be modified with a detectable moiety, such as biotin, to which another molecule can specifically bind, such as streptavidin. A variety of detectable moieties are well known to those skilled in the art. Throughout the assays, incubation and/or washing steps may be required after each combination of reagents. Incubation steps can range from about 5 seconds to several hours, optionally from about 5 minutes to about 24 hours. However, the incubation time will depend upon the assay format, antigen, solution volume, concentrations, and the like. Usually, the assays are carried out at ambient temperature, although they can be conducted at a range of temperatures.

The particular label or detectable group used in the assay is not a critical aspect of the invention, as long as it does not significantly interfere with the specific binding of the antibody used in the assay. The detectable group can be any material having a detectable physical or chemical property. Such detectable labels have been well developed in the field of immunoassays and, in general, most labels useful in such methods can be applied to the present invention. Thus, a label is any composition detectable by spectroscopic, photochemical, biochemical, immunochemical, optical, electrical, flow cytometry, or chemical means. Useful labels in the present invention include magnetic beads, fluorescent dyes, radiolabels, enzymes (e.g., horseradish peroxidase, alkaline phosphatase and others commonly used in an ELISA), and calorimetric labels such as colloidal gold or colored glass or plastic beads (e.g., polystyrene, polypropylene, latex, etc.). The label can be coupled directly or indirectly to the desired component of the assay according to methods well known in the art. Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally, simple calorimetric labels may be detected simply by observing the color associated with the label.

The measurement of the level of CAS polypeptides in body fluids also can be used to diagnosis or screen the metastatic cancers. Detection of the CAS polypeptides can involve quantitative or qualitative detection of the polypeptide and can involve an actual comparison with a control value or, alternatively, may be performed in such a way that the detection itself inherently indicates an increased level. In a one embodiment, assays for a CAS polypeptide in the body fluids are conducted under conditions wherein the level of CAS polypeptide, i.e., a level typical of a non-metastatic cancer sample, is lower than that of the metastatic cancer sample. In such assays, therefore, the detection of any CAS polypeptide in the body fluids indicates a diagnostic presence, or increased level. As described below, any of a number of methods can be used to detect CAS. A CAS polypeptide can be detected by detecting a CAS polypeptide itself, or by detecting CAS protein activity. Detection can involve quantification of the level of CAS (e.g., polypeptide level, protein level, or protein activity), or, alternatively, can be a qualitative assessment of the level, or of the presence or absence, of CAS, in particular in comparison with a control level. Any of a number of methods can be used to detect any of the above, as described infra.

The invention also provides a kit for detecting metastasis of cancers in body fluids from a mammal, which comprises CAS specific antibodies.

For use in detection and diagnostic applications suggested above, a kit is also provided by the invention. In the diagnostic or detection applications such kits may include any or all of the following: assay reagents, buffers, CAS specific antibodies, or chemicals, polypeptide, and other molecules that can bind with CAS protein or CAS polypeptide and can then reveal the level of CAS protein or CAS polypeptide in body fluids.

In addition, the kits may include instructional materials containing directions (i.e., protocols) for the practice of the methods of this invention. While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media may include links to Internet sites that provide such instructional materials.

EXAMPLE

Testing Materials and Methods
Antibodies

Antibodies used in the examples were mouse anti-CAS antibody (clone 24) (BD Pharmingen, San Diego, Calif., USA); goat anti-CAS antibody (C-20) and rabbit anti-MMP-2 antibody (H-76) (Santa Cruz Biotechnology, Santa Cruz, Calif., USA); rabbit anti-CAS antibody (AP1935) (Abgent, San Diego, Calif., USA); mouse anti-β-actin antibodies (Ab-5) (Lab Vision, Fremont, Calif., USA); goat anti-mouse (or anti-rabbit) IgG secondary antibody coupled to Alexa Fluor 488 (or Alexa Fluor 568) (Molecular Probes, Eugene, Oreg., USA).

Vectors

We isolated total cellular RNA from HT-29 human colorectal cancer cells with the Trizol reagent (Invitrogen, Carlsbad, Calif., USA). Reverse transcription reaction was carried out using the 1st-strand cDNA synthesis kit (Clontech Laboratories, Palo Alto, Calif., USA). The reverse transcription reaction mixture (20 μl) containing 1 μg of DNase-treated total RNA, 20 pmol oligo $(dT)_{18}$ primer, 50 mM Tris-HCl pH 8.3, 75 mM KCl, 3 mM $MgCl_2$, 0.5 mM each of dNTP, 1 unit RNase inhibitor, and 200 units/μg RNA of MMLV reverse transcriptase was incubated at 42° C. for 1 hour. The PCR reactions were done in a 50-μl reaction mixture containing 5 μl of the reverse transcription reaction mixture, 100 ng each of primer, 0.3 mM Tris-HCl pH 8.0, 1.5 mM KCl, 1 μM EDTA, 1% glycerol, 0.2 mM each of dNTP, and 1 μl of 50× Advantage 2 polymerase mix (Clontech). Primers used to amplify CAS cDNA (GenBank accession no. U33286) were 5'-TATAGCAATGGAACTCAGCGATGC (SEQ ID NO:3) (sense) and 5'-AGTTTAAAGCAGTGTCACACTGGC (SEQ ID NO:4) (antisense). The DNA was amplified in a GeneAmp PCR System 9700 (Perkin-Elmer, Norwalk, Conn. USA) for 35 cycles using the following parameters: 94° C. for 30 seconds, 65° C. for 30 seconds, and 72° C. for 200 seconds with a final extension step at 72° C. for 10 minutes. The amplified products were resolved in 1% agarose gel with ethidium bromide. The DNA was eluted and cloned into pGEM-T vector (Promega Corporation, Madison, Wis., USA), and was subsequently cloned into the pcDNA3.1 eukaryotic expression vector (Invitrogen) to obtain pcDNA-CAS vector. The pcDNA-CAS vector was cut with Apa I and Hind III, and the 516-bp CAS fragment (bp 1 to 516) was cloned into the Apa I and Hind III sites of pcDNA3.1 vector in an antisense direction to obtain pcDNA-anti-CAS vector. The identities of the DNA sequences were determined by DNA sequencing.

Cells and DNA Transfections

MCF-7 breast cancer cells, HT-29 human colorectal cancer cells, and B16-F10 melanoma cells were obtained from the American Type Culture Collection (Manassas, Va., USA). Cells were cultured in Dulbecco's modified Eagle's medium (DMEM) supplemented with 10% heat-inactivated fetal bovine serum (FBS), 100 units/ml penicillin, 100 μg/ml streptomycin, and 2 mM glutamate at 37° C. under a humidified 5% $CO_2$ atmosphere. Cells were transfected with vectors using the Lipofectamine plus reagent (Invitrogen). Transfected cells were selected with a high concentration of G418 for 3 weeks. Multiple drug-resistant colonies (>100) were pooled together and amplified in mass culture. The transfected cells were maintained in media containing 200 μg/ml G418. For the experiments, cells were cultured in media without G418. MCF-CAS cells, a pcDNA-CAS vector-transfected MCF-7 cell line; MCF-anti-CAS cells, a pcDNA-anti-CAS vector-transfected MCF-7 cell line; MCF-EV cells, a pcDNA3.1 empty vector-transfected MCF-7 cell line; B16-CAS cells, a pcDNA-CAS vector-transfected B16-F10 cell line; B16-anti-CAS cells, a pcDNA-anti-CAS vector-transfected B16-F10 cell line; B16-EV cells, a pcDNA3.1 empty vector-transfected B16-F10 cell line; were previously established (Liao et al., 2008b; Liao et al., 2008c).

Immunoblotting

Cells were washed with PBS and harvested by scraping. The harvested cells were washed with PBS and lysed in RIPA buffer (25 mM Tris-HCl [pH 7.2], 0.1% SDS, 0.1% Triton X-100, 1% sodium deoxycholate, 150 mM NaCl, 1 mM EDTA, 1 mM sodium orthovanadate, 1 mM phenylmethyl-sulfonyl fluoride, 10 μg/ml aprotinin, and 5 μg/ml leupeptin). The protein concentrations were determined with a BCA protein assay kit (Pierce, Rockford, Ill., USA). Fifty micrograms of each protein sample was loaded onto SDS-polyacrylamide gel. Proteins were transferred to nitrocellulose membranes (Amersham Pharmacia, Buckinghamshire, UK). The membrane was blocked at 4° C. for overnight with blocking buffer (1% BSA, 50 mM Tris-HCl, pH 7.6, 150 mM NaCl, 0.1% Tween-20). The blots were incubated for 1 hour at room temperature (RT) with primary antibodies followed by incubating with secondary antibodies conjugated to horseradish peroxidase for 1 hour. The levels of protein were detected by enhanced chemiluminescence with an ECL Western blotting detection system (Amersham Pharmacia).

Immunofluorescence

Cells grown on coverslips (12×12 mm) were cytospun at 1000 rpm for 10 minutes. Cells were washed with PBS, fixed with 4% paraformaldehyde, permeabilized with 0.1% Triton X-100 in 4% paraformaldehyde, and blocked with PBS containing 0.1% BSA and 0.5% Tween-20. Cells were incubated with primary antibodies, washed with PBS, incubated with goat anti-mouse (or anti-rabbit) IgG secondary antibodies coupled to Alexa Fluor 488 (or 568). Coverslips were examined with a Zeiss Axiovert 200M inverted fluorescence microscope. Experiments were carried out on duplicate coverslips of three independent experiments and five random fields were imaged per coverslip.

MMP-2 and CAS Secretion Analyses

Equal numbers of cells were seeded onto 100-mm culture dishes. Fetal bovine serum (FBS) contains a high level of endogenous MMP-2 and may have interfered with the MMP-2 secretion assay; FBS may also have interfered with the assay of CAS in immunoblotting. Thus, cells were grown to sub-confluence, washed with phosphate-buffered saline (PBS), then changed to media without serum supplementation and incubated for 36 h. The conditioned media were collected. To remove any possible suspended cells or cell debris, the conditioned media were centrifuged at 10,000 rpm for 10 min, and supernatants were harvested. Cell numbers were determined and the cell number-standardized conditioned media were subjected to immunoblotting with anti-MMP-2 antibody and anti-CAS antibody.

Matrigel-Based Invasion Assay

Polyvinylpyrrolidone-free polycarbonate filters with 8-μm pore size (Costar, Cambridge, Mass., USA) were soaked in matrigel (BD Biosciences) (1:10 in DMEM for transfected B16-F10 cells and 1:50 in DMEM for transfected MCF-7 cells) at 4° C. for 36 hours and then incubated at 37° C. for 2 hours. The filters were washed 4 times with DMEM and were placed in the microchemotaxis chambers. The cells were treated with 0.1% trypsin-EDTA, re-suspended in DMEM media containing 10% FBS and then washed with serum-free DMEM media. Cells ($1 \times 10^5$) were finally suspended in DMEM (200 μl) and placed in the upper compartment of the chemotaxis chambers. Culture medium (300 μl) containing 20% FBS was placed in the lower compartment of the chemotaxis chamber to serve as a source of chemoattractants. After being incubated in the cell culture incubator for 10 hours (for transfected B16-F10 cells) or 24 hours (for transfected MCF-7 cells), the cells on the upper surface of the filter were completely wiped away with a cotton swab. The cells on the lower surface of the filter were fixed in methanol, stained with Liu's A and Liu's B reagents, and then counted under a microscope. Cells invaded to the microchemotaxis chambers were also counted. For each replicate, the tumor cells in 10 randomly selected fields were determined, and the counts were averaged.

Animal Metastasis Experiment

C57BL/6 mice between 6-7 weeks old (National Laboratory Animal Center, Taipei, Taiwan) were housed in an animal holding room under standard conditions (22° C.; 50% humidity; 12-hours light/dark cycle). Each C57BL/6 mouse was injected with viable B16-EV cells or B16-anti-CAS cells ($5 \times 10^4$ cells in 50 μl DMEM/mouse) in the tail vein. Each experimental group included 11 B16-EV cells-injected mice and 11 B16-anti-CAS cells-injected mice, and totally 66 mice were used in the experiment. Twenty-five days after injection, the mice were sacrificed and necropsied. The numbers of tumors in lungs were counted by macrography and micrography. Mouse care and experimental procedures were performed following the guideline of the Animal Care Committee of Academia Sinica, Taiwan.

Immunohistochemistry

Immunohistochemistry was performed on 3-μm formalin-fixed/paraffin-embedded cancer tissue sections. After deparaffinization in xylene and rehydration in graded ethanol, the sections were immersed in citrate buffer (pH 6.0) at 95° C. for 10 min. Immunohistochemical detection was performed with the use of a labeled streptavidin-biotin method with a Histostain kit (Zymed, San Francisco, Calif., USA). Endogenous peroxidase activity was blocked with 3% hydrogen peroxide in water, and then nonspecific staining was blocked by incubation with 5% BSA for 1 h at room temperature. Sections were incubated with a 50-fold dilution of anti-CAS antibodies (clone 24) for 1 h at room temperature and then reacted with biotinylated secondary antibodies, and finally with peroxidase-labeled streptavidin. Sections were developed with diaminobenzidine, washed with distilled water, and counterstained with Mayer's hematoxylin.

Serum Samples (1) Serum samples other than the colorectal cancer serum samples. Serum samples from 47 healthy individuals were obtained with informed consent. The mean age of the healthy individuals was 58.5±11.6 years (mean±S.D., range 17-79 years). Cancer serum samples other than the colorectal cancer serum were obtained from 90 cancer patients admitted to Tungs' Taichung MetroHarbor Hospital, Taiwan at the time of diagnosis following informed consent using Institutional Review Board-approved guidelines. These cancer cases included 39 primary cancers (mean age 53.2±15.8, range 21-81 years), 25 invasive cancers (mean age 51.3±16.6, range 43-84 years), and 26 metastatic cancers (mean age 59.1±12.3, range 38-78 year). All of the cases with metastatic cancer we studied were pathologically diagnosed of having distal metastases of tumors to other organs or metastases of tumors to the lymph nodes.

(2) Colorectal cancer serum samples. Colorectal cancer serum samples were obtained from 57 colorectal cancer patients admitted to Changhua Christian Hospital at the time of diagnosis with informed consent using Institutional Review Board-approved guidelines. The baseline characteristics of the patients are shown in Table 1. These cancer cases included 27 non-metastatic colorectal cancer patients (11 males, 16 females) and 30 metastatic colorectal cancers patients (15 males, 15 females). The mean age of patients was 62.9±15.7 years (mean±S.D., range 27-91 years) for the non-metastatic group and was 64.21±16.7 years (range 26-94 years) for the metastatic group. Tumors were classified according to the tumor-node-metastasis (TNM) classification of colorectal cancer. Of the primary tumors, 3.7% were Tis, 11.1% were T1, 33.3% were T2, 51.9% were T3, and 0% were T4 for the non-metastatic group; and 0% were Tis, 6.7% were T1, 6.7% were T2, 80.0% were T3, and 6.7% were T4 for the metastatic group. According to the TNM classification, all of these non-metastatic cancers were N0M0. In the metastatic group, 3.3% were N0, 50.0% were N1, and 46.7% were N2 in the lymphoid node metastasis examination and 73.3% were M0 and 26.7% were M1 in the distant metastasis examination.

TABLE 1

Baseline characteristics of the colorectal cancer patients

| Clinicopathological parameter | Non-metastatic (n = 27) | Metastatic (n = 30) |
|---|---|---|
| Mean age (range), year[a] | 62.9 ± 15.7, 27-91 | 64.21 ± 16.7, 26-94 |
| Gender | | |
| Male | 11 | 15 |
| Female | 16 | 15 |
| Primary tumor (T) | | |
| Tis | 1 | 0 |
| T1 | 3 | 2 |
| T2 | 9 | 2 |
| T3 | 14 | 24 |
| T4 | 0 | 2 |
| Stage | | |
| 0 | 1 | 0 |
| I | 12 | 0 |
| II | 14 | 0 |
| III | 0 | 22 |
| IV | 0 | 8 |
| Lymph node and distant metastasis[b,c] | | |
| N0M0 | 27 | 0 |
| N1M0 | 0 | 12 |
| N2M0 | 0 | 10 |

TABLE 1-continued

Baseline characteristics of the colorectal cancer patients

| Clinicopathological parameter | Non-metastatic (n = 27) | Metastatic (n = 30) |
|---|---|---|
| N0M1 | 0 | 1 |
| N1M1 | 0 | 3 |
| N2M1 | 0 | 4 |

[a]Mean ± SD.
[b]N0, no regional lymph node metastasis; N1, metastasis in 1-3 regional lymph nodes; N2, metastasis in ≧4 regional lymph nodes; M0, no distant metastasis; M1, distant metastasis.
[c]All of these M1 cases were distant metastases of colorectal cancers to the liver.

Serum samples were collected by allowing the blood to sit at room temperature for a minimum of 30 min to allow clots to form. Samples were then centrifuged at 1300 g at 4° C. for 20 min and the sera were harvested and stored at −80° C. All samples were labeled with a unique identifier to protect the confidentiality of the patients. None of the samples was thawed before analysis. To remove any possible suspended cells or cell debris in the sera, samples were centrifuged at 10,000 rpm for 10 min, and supernatants were harvested. The supernatants were subjected to ELISA or immunoblotting to analyze CAS.

GST-CAS Fusion Protein Production and CAS Protein Purification

GST-CAS fusion protein production and CAS purification. The GST-CAS fusion protein expression vector was constructed by PCR amplification of the restriction enzyme-linearized pcDNA-CAS vector with the primers GGATCCATGGAACTCAGCGATGCAAATCTG (SEQ ID NO:5) (sense, BamH I site is underlined) and CTCGAGTTAAAGCAGTGTCACACTGGCTG (SEQ ID NO:6) (antisense, Xho I site is underlined). The amplified products were sub-cloned into the BamH I and Xho I sites of pGEX-4T-1 vector (Amersham Pharmacia) to obtain the pGEX-CAS vector. The identity of DNA sequences was examined by DNA sequencing. The pGEX-CAS vector was transformed into the E. coli Rosetta (DE3) pLysS strain. The transformed E. coli was cultured to O.D.600=1.2, and the GST-CAS fusion protein was then induced with 0.1 mM isopropyl-beta-D-thiogalactopyranoside (IPTG) for 5 h. Fusion proteins were purified by glutathione-Sepharose 4B beads using the Bulk GST Purification Modules (Amersham Pharmacia). GST protein (without CAS fusion protein) produced by growing pGEX-4T-1 vector-transformed bacteria was purified by standard techniques and was used as a control. The bound affinity column was then washed with PBS before being eluted with reduced glutathione (Amersham Pharmacia). GST-CAS fusion protein was cleaved with thrombin (3 units/100 μg of fusion protein) (Sigma Chemicals, St Louis, Mo., USA) at 22° C. for 16 h. The thrombin and GST were removed using the Amicon® Ultra-4 Centrifugal Filter Units (Millipore, Billerica, Mass., USA). The purified CAS protein was identified by immunoblotting with anti-CAS antibodies. The concentration of CAS protein was determined with a BCA protein assay kit (Pierce, Rockford, Ill., USA) and the purified CAS proteins were used as the standards in the ELISA assays for determining the cut-off value of serum CAS of patients with metastatic cancers.

ELISA

Anti-CAS (C-20 or clone 24) antibody-coated 96-well plates (Costar) were blocked with 5% BSA in PBS for 1 hour. Wells were washed with PBS, and then incubated with serum samples (3-fold dilution with PBS) for 1 hour. After washing with PBST (0.05% Tween-20 in PBS), wells were incubated with biotin-conjugated rabbit anti-CAS antibodies for 1 hour. The biotin-conjugated rabbit anti-CAS antibodies was prepared by biotinylating the rabbit anti-CAS polyclonal antibody (AP1935) using the Biotin Labeling Kit-NH2 according to the manufacturer's protocol (Dojindo Laboratories, Kumamoto, Japan). Wells were washed with PBST and then reacted with streptavidin-conjugated horseradish peroxidase (R&D Systems, Minneapolis, Minn.), followed by incubation with substrate reagent (R&D Systems). For calibration, three blank wells containing PBS were used as the background value, and three wells that were not coated with the anti-CAS antibodies but did react with all other ELISA reagents were used as the control wells. The absorbance at 450 nm was measured within 30 min with a Thermo Multiskan EX Microplate Photometer (Thermo Fisher Scientific, Waltham, Mass.). The O.D. value of the sample well that was higher than the highest O.D. value of the control wells was considered to be positive for serum CAS. Each sample was assayed two times, the C-20 anti-CAS antibody was used in the first assay, and the clone 24 anti-CAS antibody was used in the second assay. The results of the two assays were very similar, indicating the accuracy of our assay.

Assay of Serum CEA Level

CEA values of the samples were measured using the Architect CEA Reagent kit (Abbott Laboratories, Abbott Park, Ill.) in accordance with the manufacturer's instructions. According to the instructions, a CEA value of ≧5 ng/ml was considered as pathologically positive.

Statistical Analysis

Data were analyzed by using the SPSS 14.0 statistic software. Statistical differences were analyzed by two-tailed Fisher's exact test. An α-level of 0.05 was used to determine statistical significance.

Example 1

Vesicle-Like Staining of CAS Protein in Cytoplasmic Areas Near the Cell Membrane and Cell Protrusions of MCF-7 Cells The distributions of CAS in MCF-7 cells were studied by immunofluorescence microscopy. CAS can associate with microtubules (Scherf et al., 1996) and importin-α (Kutay et al., 1997), a nuclear-transport receptor. Thus, CAS should show granule-like staining in the perinuclear areas of cells due to its association with importin-α, or show microtubule-like staining due to its association with microtubules. However, in addition to granule-like staining in the cytoplasm surrounding perinuclear areas, CAS also showed vesicle-like staining in the cell protrusion of MCF-7 cells. FIG. 1 shows the cellular distribution of CAS analyzed by immunofluorescence with the clone 24 anti-CAS monoclonal antibody. Note the vesicle-like staining of CAS (arrows) in the cell protrusions of cells marked with X1 and X2. The scale bar indicates 30 μm. Cytoplasm vesicles play an important role in regulating the exocytosis and secretion of cells (Pickett et al., 2006). Thus, the vesicle-like staining of CAS in cell protrusion indicates that CAS might play a role in regulating the secretion of cells.

Example 2

CAS Expression Regulates the Distribution of MMP-2 in the Tip and Edge Ends of the Cell Protrusions of MCF-7 Cells MMP-2 is a secretory protein. The effect of CAS expression on the cellular distribution of MMP-2 was studied by double-stain immunofluorescence. MMP-2 is known to be located in cytoplasm. In addition to being localized in cytoplasm, our data showed that MMP-2 was also distributed in the nuclei of MCF-7 cells (FIG. 2B). MMP-2 has been shown to be present in the nuclei of cardiac myocytes, and this was correlated with the cleavage of poly (ADP-ribose) polymerase (Kwan et al., 2004). Thus, it is reasonable that MMP-2 would also be stained in the nuclei of MCF-7 cells in our study. MCF-7 cells were separately transfected with the pcDNA3.1 empty vector, pcDNA-CAS vector, and pcDNA-anti-CAS vector to obtain MCF-EV, MCF-anti-CAS, and MCF-CAS cells, respectively (FIG. 2). In MCF-anti-CAS cells, rare colocalization of CAS with MMP-2 was found in the cell protrusions; at the same time, much colocalization of CAS with MMP-2 was found in the tips or edge ends of the cell protrusions of MCF-CAS cells (FIG. 2B). These results indicated that CAS is associated with MMP-2-containing vesicle and increased CAS expression facilitates the translocation of MMP-2-containing vesicles to the cell protrusions. FIG. 2A shows the expression of CAS in MCF-EV, MCF-CAS, and MCF-anti-CAS cells analyzed by immunoblotting with anti-CAS antibody. FIG. 2B shows immunofluorescence analysis of CAS and MMP-2 distributions in MCF-EV, MCF-CAS, and MCF-anti-CAS cells. Arrows indicate some of the cell protrusions of MCF-EV, MCF-CAS, and MCF-anti-CAS cells. Please note the increased distribution of CAS and MMP-2 in the tip or edge ends of the cell protrusions of MCF-CAS cells, and decreased distribution of CAS and MMP-2 in the tip or edge ends of the cell protrusions of MCF-anti-CAS cells. The scale bar represents 20 μm. The brightness and contrast of the fluorescence in the photo were strengthened to emphasize the colocalization of CAS with MMP-2-containing vesicle in the tip or edge ends of cell protrusions.

Example 3

Colocalization of CAS with MMP-2 in Vesicles Surrounding the Outside of Cell Membrane In a high-resolution photograph, colocalization of CAS with MMP-2 was observed in the cytoplasmic areas near cell membrane as well as in the cell protrusions of MCF-CAS cells (FIG. 3). In particular, some CAS was colocalized with MMP-2 in vesicles surrounding the outside of cell membrane (FIG. 3, arrows). Because MMP-2 is a secretory protein, these results possibly indicated that CAS was secreted together with MMP-2. Thus, CAS may also be a secretory protein. FIG. 3 shows colocalization of CAS with MMP-2 in vesicles surrounding the outside of MCF-7 cell membrane analyzed by immunofluorescence with anti-CAS antibody and anti-MMP-2 antibody. Note the colocalization of CAS with MMP-2 in vesicles surrounding the outside of cell membrane (arrows). The scale bar represents 30 μm. The brightness and contrast of the fluorescence in the photo were strengthened to emphasize the colocalization of CAS with MMP-2-containing vesicle in vesicles surrounding the outsides of cell membrane.

Example 4

CAS Expression Regulates the Invasion of B16-F10 Melanoma Cells

B16-F10 melanoma cells, a highly metastatic cancer cell line, were separately transfected with the empty pcDNA3.1 vector, pcDNA-CAS vector, and pcDNA-anti-CAS vector to obtain B16-EV cells, B16-CAS cells, and B16-anti-CAS cells, respectively (FIG. 4A). The results of MMP-2 secretion assays showed that increased CAS expression enhanced MMP-2 secretion, and reduced CAS expression decreased MMP-2 secretion from B16-F10 melanoma cells (FIG. 4B). Matrigel-based invasion assays showed that increased CAS expression enhanced the invasion of B16-F10 cells by 249.2% (P=0.0019), and reduced CAS expression inhibited the invasion of B16-F10 cells by 75.7% (P=0.0073). The average numbers of the invaded cells were 89.5±10.7, 35.9±9.4, and 8.7±2.2 (cells/field) for B16-CAS, B16-EV, and B16-anti-CAS cells, respectively (FIG. 4C). Thus, the results of matrigel-based invasion assay indicate that CAS can regulate the invasion of cancer cells. FIG. 4 shows CAS expression regulates the invasion of B16-F10 melanoma cells. (A) Analyses of CAS expression in B16-EV, B16-CAS cells, and B16-anti-CAS cells by immunoblotting with anti-CAS antibodies. (B) Immunoblotting analyses of conditioned media collected from B16-EV, B16-CAS cells, and B16-anti-CAS cells with anti-MMP-2 antibodies. The immunoblotting assays were repeated three times and showed similar results; a representative immunoblot is shown here. (C) Matrigel-based invasion assays of B16-EV, B16-CAS cells, and B16-anti-CAS cells. The upper is a representative photograph of the invaded cells. Data are represented as the mean of three independent experiments. $^{\#1}$P=0.0019, compared to that of the B16-EV cells. $^{\#2}$P=0.0073, compared to that of the B16-EV cells.

Example 5

Reduced CAS Expression Decreased the Pulmonary Metastasis of B16-F10 Cells

Experimental animal tumor metastasis assays were done to study the effect of CAS expression on the metastasis of B16-F10 melanoma cells. B16-F10 cells are high metastatic in C57BL/6 mice, thus we studied whether CAS reduction could reduce the metastasis of B16-F10 cells in C57BL/6 mice. FIG. 5 show that reduced CAS expression decreased the pulmonary metastasis of B16-F10 cells in C57BL/6 mice. Table 2 describes the animal tumor metastasis experiments showing that reduced CAS expression decreased the pulmonary metastasis of B16-F10 cells by 56% in C57BL/6 mice (P=0.0107). The average lung tumor numbers of mice injected with B16-EV cells were 32.7±6.5 tumors/mouse (average tumor diameter 2.6±1.8 mm) and were 14.3±4.6 tumors/mouse (average tumor diameter 2.5±1.5 mm) for mice injected with B16-anti-CAS cells. Anti-CAS transfection reduced the mortality of mice injected with B16-F10 cells; probably due to anti-CAS transfection reduces the metastasis ability of B16-F10 cells. The results showed that reduced CAS expression inhibited the pulmonary tumor metastasis of B16-F10 melanoma cells in C57BL/6 mice.

TABLE 2

CAS regulates the metastasis of B16-F10 melanoma cells

| Experimental groups | B16-EV cells-injected mice (n = 19) | B16-anti-CAS cells-injected mice (n = 24) |
|---|---|---|
| Average tumor diameter (mean ± SD) (mm) | 2.6 ± 1.8 | 2.5 ± 1.5 |
| Average lung tumor numbers (mean ± SD) tumors/mouse | 32.7 ± 6.5 | 14.3 ± 4.6 * |

In the experiment, each experimental group included 11 B16-EV cells-injected mice and 11 B16-anti-CAS cells-injected mice, and totally 66 mice were used in the study. Each C57BL/6 mouse was injected with viable B16-EV cells or B16-anti-CAS cells ($5\times10^4$ cells in 50 µl DMEM/mouse) in the tail vein. Eleven B16-EV cells-injected mice and six B16-anti-CAS cells-injected mice passed away three weeks after injection. Eleven B16-EV cells-injected mice and six B16-anti-CAS cells-injected mice passed away three weeks after injection thus were excluded from the statistics. Six mice (three B16-EV cells-injected mice and three B16-anti-CAS cells-injected mice) didn't grow tumor in lungs and thus were also excluded from the statistics. The results showed that reduced CAS expression inhibited the pulmonary tumor metastasis of B16-F10 melanoma cells in C57BL/6 mice by 56% in C57BL/6 mice. *P=0.0107, compared to that of the B16-EV cells-injected mice.

Example 6

CAS is a Secretory Protein and the Presence of Secretory CAS in Sera of Patients with Metastatic Cancer We assayed whether CAS is also a secretory protein by immunoblotting. Fetal bovine serum (FBS) contains various proteins and substances and may have interfered with our assay. Thus, B16-F10 melanoma cells were grown to sub-confluence, washed with PBS, and changed to medium with no FBS. The results showed that CAS was present in the conditioned medium of serum-starved B16-F10 cells (FIG. 6A). Furthermore, the results of immunoblotting showed that the level of secretory CAS was higher in the conditioned medium of serum-starved B16-CAS cells than in that of B16-EV cells (FIG. 6B). These results indicated that CAS is also a secretory protein, and increased CAS expression in cells could enhance CAS secretion.

Serum samples collected from healthy donors and patients with primary cancers, invasive cancers, or metastatic cancers were also examined for the presence of CAS protein in the sera. All of the metastatic cancer cases that we studied were pathologically diagnosed of having distal metastases of tumors to other organs or metastases of tumors to the lymph nodes. Although other unknown proteins or substances contained in human sera might also have interfered with CAS detection, the CAS protein bands were still detected by the immunoblotting assay (FIG. 6A). The results showed that CAS was obviously present in the sera of patients with metastatic cancer and was only slightly present in the sera of patients with invasive cancer (FIGS. 6A and C). FIG. 6 shows that CAS is a secretory protein and the presence of CAS protein in sera of patients with metastatic cancer. (A) Immunoblotting analyses of serum samples collected from patients with metastatic cancer with anti-CAS antibodies. Thirty microliters of each serum sample and 60 µl of each conditioned medium supplemented with or without FBS collected from B16-F10 cells were applied in the assay as indicated. A well loaded with the total cell lysate of B16-F10 cells was used for the control. Note that secretory CAS was detectable in the sera of patients with metastatic cancer and the conditioned medium of serum-starved B16-F10 cells. (B) Enhanced CAS expression increased the secretion of CAS in the medium. Conditioned media collected from serum-starved B16-EV and B16-CAS cells were subjected to immunoblotting with anti-CAS antibodies. (C) Immunoblotting analyses of CAS levels in sera collected from healthy donors and patients with metastatic cancer, invasive cancer, or primary cancer with anti-CAS antibodies. Each immunoblotting assay was repeated three times and showed similar results; representative immunoblots are shown here.

In assaying the presence of secretory CAS, the serum samples and the conditioned media were centrifuged at 10,000 rpm for 10 min, the supernatants were harvested, and only the supernatants were used in the study. Thus, it is not possible that the presence of secretory CAS was due to contamination by suspended cells or cell debris in the samples. The CAS protein bands in the immunoblots were very intense especially those of samples of conditioned media. The molecular weight of CAS is about 110 kDa (Scherf et al., 1996). The molecular weight of the CAS protein in the conditioned media and sera of cancer patients was also about 110 kDa. Thus, it is also not possible that the CAS protein we identified had come from CAS protein released from broken or lysed cells present in the conditioned media or sera of metastatic cancer patients.

Example 7

CAS is Positively Stained in the Stroma and Gland Lumen of Metastatic Cancer Tissues Immunohistochemistry analyses of metastatic breast and colorectal cancer tissues with the clone 24 anti-CAS monoclonal antibody showed that CAS was mainly distributed in the cytoplasm of ductal gland cells in metastatic breast cancer tissue and the cytoplasm of gland cells in metastatic colorectal cancer tissue (FIG. 7). CAS was also positively stained in the stroma of cancer tissues (FIG. 7, arrowheads). Importantly, CAS was also positively stained in the ductal lumen of metastatic breast cancer tissue and the gland lumen of metastatic colorectal cancer tissue (FIG. 7, arrows). FIG. 7 shows the distribution of CAS protein in metastatic cancer tissues. Distributions of CAS in the metastatic colorectal (A, B, and D) and breast (C) cancer tissues were analyzed by immunohistochemistry with the anti-CAS monoclonal antibody. Note the positive staining of CAS in the stroma (A and B, arrowheads), ductal lumen (C, arrows), and gland lumen (D, arrows) of cancer tissues. The scale bar represents 50 µm. The presences of CAS in the ductal lumen of metastatic breast cancer tissue and gland lumen of metastatic colorectal cancer tissue indicate that CAS protein is secretory in metastatic cancers. The tumor microenvironment, or stroma, consists of extracellular matrix and plays an important role in regulating cancer metastasis (Zigrino et al., 2005). Thus, positive staining of CAS in the stroma of metastatic cancer tissues indicates that CAS is secreted into the stroma of cancer tissues and regulates cancer metastasis. The glands of cancer tissues also provide metastatic cancer cells a way to invade the adjacent tissue or other organs. The positive staining of CAS in cancerous gland cells indicates that CAS may play an important role in the secretion of cancerous tissues and regulation of cancer metastasis. Also, substances that are secreted from a gland lumen of a cancer tissue ultimately may reach the blood vessels (Brandtzaeg et al., 1987; Pieper-Bigelow et al., 1990). Our data showed that CAS was positively stained in the gland lumen of metastatic cancer tissues. Thus, it is reasonable that CAS could be detected in the sera of patients with metastatic cancers.

Example 8

Higher Prevalence of CAS Protein in Sera of Patients with Metastatic Cancer

ELISA assays were performed to study the prevalence of serum CAS in the sera of patients with metastatic, invasive, or primary cancers. The results showed that the prevalence of serum CAS were 57.7% (15/26), 32.0% (8/25), and 5.1% (2/39) for patients with metastatic, invasive, and primary cancers, respectively (FIG. 8A). The prevalence of serum CAS detected in healthy donors was 6.4% (3/47) (FIG. 8A). The P-values were <0.01 between the metastatic cancer group and healthy donor group, <0.01 between the metastatic cancer group and primary cancer group, <0.05 between the metastatic cancer group and invasive cancer group, <0.05 between the invasive cancer group and healthy donor group, and 0.685 between the primary cancer group and healthy donor group. With the use of the purified CAS protein as the standard, the cut-off value of CAS in the sera of patients with metastatic cancer was determined to be $\geq 3$ ng/ml. The presence of secretory CAS in the sera of patients with metastatic cancer was not restricted to a specific cancer type. For the metastatic cancer types, the ratios of serum CAS detected were 75% (6/8) of breast cancers, 75% (3/4) of lung cancers, 75% (3/4) of cervical cancers, 100% (1/1) of cholangiocarcinoma, 100% (1/1) of lip cancers, 50% (1/2) of hypopharyngeal cancers, 0% (0/2) of esophageal cancers, 0% (0/1) of ovarian cancers, 0% (0/1) of parotid cancers, 0% (0/1) of oviduct omental cancers, and 0% (0/1) of buccal cancers (FIG. 8B). These results show a higher prevalence of CAS in the sera of patients with metastatic cancer, and thus CAS may be useful as a serological marker for metastatic cancer screening.

FIG. 8 shows a higher prevalence of secretory CAS in sera of patients with metastatic cancer. (A) The prevalences of serum CAS in healthy donors and patients with primary, invasive, and metastasis cancers were determined by ELISA. # Significant difference between the metastatic cancer group and primary cancer group (P<0.01). (B) Metastatic cancer types and the ratio of serum CAS detected in the metastatic cancers. The numbers of serum CAS-positive cases of each cancer type to the total numbers of each metastasis cancer type are indicated.

In the assay of CAS protein level with ELISA, the serum samples were centrifuged at 10,000 rpm for 10 min, the supernatants were harvested, and only the supernatants were used in the study. Thus, it is not possible that the presence of secretory CAS protein was due to contamination by suspended cells or cell debris in the samples.

Example 9

Positive Staining of CAS Protein in the Gland Lumen of Metastatic Colorectal Cancer Tissues Immunohistochemistry with the clone 24 anti-CAS monoclonal antibodies and the tissue sections of metastatic colorectal cancer lumps showed that CAS protein was mainly distributed in the cytoplasm of cells in colorectal glands (FIG. 9). CAS protein was also positively stained in the stroma of metastatic colorectal cancer tissues (FIG. 9, arrowheads). Importantntly, CAS protein was also positively stained in the gland lumen of colorectal cancer tissues (FIG. 9, arrows), indicating the CAS protein may be secreted from the colorectal cancer tissues. FIG. 9 shows the distributions of CAS protein in metastatic colorectal cancer tissues analyzed by immunohistochemistry. Note the positive staining of CAS protein in the stroma (arrowheads) and the gland lumen (arrows) of metastatic colorectal cancer tissues. The scale bar represents 50 µm. Glands are secretory organs, thus this result indicates that CAS may play a role in the secretion of colorectal cancer glands. The presence of CAS in the stroma, cytoplasm of gland cells, and gland lumen of metastatic colorectal cancer tissues indicate that CAS is secretory in metastatic colorectal cancers and CAS may play an important role in the secretion of colorectal cancers as well as the metastasis of colorectal cancers.

Example 10

CAS is Present in Sera of Patients with Metastatic Colorectal Cancer

Serum samples collected from patients with metastatic colorectal cancer were subjected to immunoblotting with the clone 24 anti-CAS monoclonal antibody. The results showed that CAS was obviously present in sera of patients with metastatic colorectal cancer as the clear CAS protein bands were present in the immunoblot (FIG. 10). Thus, CAS is also a secretory protein and is present in sera of patients with metastatic colorectal cancer.

FIG. 10 shows the results of immunoblotting analyses of conditioned medium harvested from serum-starved B16-F10 cells and serum samples collected from metastatic colorectal cancer patients with the clone 24 anti-CAS monoclonal antibody. A well loaded with total cell lysate of B16-F10 cells was used as the control. Note that secretory CAS was detectable in sera of patients with metastasis cancers and the conditioned medium of the serum-starved B16-F10 cells. The immunoblotting assay was repeated three times and showed similar results; a representative immunoblot is shown here.

Example 11

Baseline Characteristics of the Colorectal Cancer Patients

Colorectal cancer serum samples were obtained from 57 colorectal cancer patients admitted to Changhua Christian Hospital at the time of diagnosis with informed consent using Institutional Review Board-approved guidelines. The baseline characteristics of the patients are shown in Table 1. These cancer cases included 27 non-metastatic colorectal cancer patients (11 males, 16 females) and 30 metastatic colorectal cancers patients (15 males, 15 females). The mean age of patients was 62.9±15.7 years (mean±S.D., range 27-91 years) for the non-metastatic group and was 64.21±16.7 years (range 26-94 years) for the metastatic group. Tumors were classified according to the tumor-node-metastasis (TNM) classification of colorectal cancer. Of the primary tumors, 3.7% were Tis, 11.1% were T1, 33.3% were T2, 51.9% were T3, and 0% were T4 for the non-metastatic group; and 0% were Tis, 6.7% were T1, 6.7% were T2, 80.0% were T3, and 6.7% were T4 for the metastatic group. According to the TNM classification, all of these non-metastatic cancers were N0M0. In the metastatic group, 3.3% were N0, 50.0% were N1, and 46.7% were N2 in the lymphoid node metastasis examination and 73.3% were M0 and 26.7% were M1 in the distant metastasis examination.

Example 12

A Comparison of Measuring Serum CAS Level and Serum CEA Level in the Diagnosis of Metastatic Colorectal Cancers Serum samples from 27 non-metastatic and 30 metastatic colorectal cancer patients were assayed for the prevalence of secretory CAS in metastatic colorectal cancers. Pathological examinations showed that all of these cases were adenocarcinomas. All of the metastatic cases were pathologically diagnosed as having distal metastases of colorectal tumors to other organs or metastasis of colorectal tumors to lymph nodes. All of the distal metastases cases were metastases to the liver. The results of the ELISA assay showed that the prevalence of CAS in the sera of metastatic colorectal cancer patients was 60.0% (18/30) and that in non-metastatic colorectal cancer patients was 14.8% (4/27) (P=0.001) (Table 3). Table 3 shows the comparison of measuring serum CAS level and serum CEA level in the diagnosis of metastatic colorectal cancers. The results show a higher prevalence of CAS protein in sera of patients with metastatic colorectal cancers. CEA is frequently used to monitor colorectal carcinoma after surgical resection, although early studies suggested that it could be used for screening colorectal cancer metastasis. The serum CEA levels of these patients were analyzed to compare the competence of CAS and CEA in diagnosing colorectal cancer metastasis. The results showed that the prevalence of pathological serum CEA cases in the sera of metastatic colorectal cancer patient was 43.3% (13/30) and in that of the non-metastatic group was 40.7% (11/27) (P=1) (Table 3). Thus, there was no significant difference in the pathological serum CEA cases between the metastatic and non-metastatic colorectal cancer groups. These results indicate that measurement of serum CAS protein should be useful for screening metastatic colorectal cancer patients.

TABLE 3

A comparison of measuring serum CAS level and serum CEA level in the diagnosis of metastatic colorectal cancers

| Groups | Non-metastatic (n = 27) | Metastatic (n = 30) |
|---|---|---|
| CAS-positive (cases, %) | 4, 14.8% | 18, 60.0%**,[a] |
| CEA-positive (cases, %) | 11, 40.7% | 13, 43.3%[b] |

[a]P = 0.001, compared to the non-metastatic group.
[b]P = 1, compared to the non-metastatic group.

Example 13

A Comparison of Measuring Serum CAS Level and Serum CEA Level in the Diagnosis of Lymph Node and Distal Metastases of Colorectal Cancers Serum samples from 27 non-metastatic and 30 metastatic colorectal cancer patients were assayed for comparing the efficiency of measuring serum CAS and serum CEA in the diagnosis of lymph node metastases and distal metastases of colorectal cancers. In the lymph node metastasis cases (i.e. N1M0 or N2M0), there was a low percentage (36.3%, 8/22) of pathological serum CEA cases in these patients (Table 4). However, there was a high percentage (62.5%, 5/8) of pathological serum CEA cases in the distal metastatic cases (i.e. N0M1, N1M1, and N2M1) (Table 4). Particularly, all of these 8 distal metastatic cases were metastasis of colorectal tumor to the liver (Table 1). These results are in accordance with the fact that high blood CEA levels in bowel cancers apparently have a relevance with patients had advanced disease with extensive metastases, especially liver involvement (Moertel et al., 1993). Comparatively, the percentage of serum CAS-positive cases in the lymph node metastasis cases (i.e. N1M0 or N2M0) was 63.6% (14/22); and the percentage of serum CAS-positive cases in the distal metastatic cases (i.e. N0M1, N1M1, and N2M1) was 50.0% (4/8) (Table 4). Thus, CAS is superior to CEA for screening the lymph node metastasis of colorectal cancers.

TABLE 4

A comparison of measuring serum CAS level and serum CEA level in the diagnosis of lymph node and distal metastases of colorectal cancers

| Groups | Lymph node metastasis[a] (n = 22) | Distal metastasis[b,c] (n = 8) |
|---|---|---|
| CAS-positive (cases, %) | 14, 63.6% s**,[d] | 4, 50%[e] |
| CEA-positive (cases, %) | 8, 36.3% | 5, 62.5% |

[a]Lymph node metastases: N0M0, N1M0, and N2M0.
[b]Distal metastases: N0M1, N1M1, and N2M1.
[c]All of these cases were the metastases of colorectal cancers to the liver.
[d]P < 0.01, compared to that of the CEA-positive cases.
[e]P = 0.087, compared to that of the CEA-positive cases.

REFERENCE

Basuyau J P, Leroy M, Brunelle P. (2001) Determination of tumor markers in serum. Pitfalls and good practice. Clin Chem Lab Med 39: 1227-1233.

Behrens P, Brinkmann U, Fogt F, Wernert N, Wellmann A. (2001). Implication of the proliferation and apoptosis associated CSE1L/CAS gene for breast cancer development. Anticancer Res 21: 2413-2417.

Behrens P, Brinkmann U, Wellmann A. (2003) CSE1L/CAS: its role in proliferation and apoptosis. Apoptosis 8: 39-44.

Bogenrieder T, Herlyn M. (2003). Axis of evil: molecular mechanisms of cancer metastasis. Oncogene 22: 6524-6536.

Boni R, Wellmann A, Man Y G, Hofbauer G, Brinkmann U. (1999) Expression of the proliferation and apoptosis-associated CAS protein in benign and malignant cutaneous melanocytic lesions. Am J Dermatopathol 21: 125-128.

Brandtzaeg P, Bjerke K, Kett K, Kvale D, Rognum T O, Scott H, Sollid L M, Valnes K. (1987) Production and secretion of immunoglobulins in the gastrointestinal tract. Ann Allergy 59: 21-39.

Brenner D E, Normolle D P. (2007) Biomarkers for cancer risk, early detection, and prognosis: the validation conundrum. Cancer Epidemiol Biomarkers Prev 16: 1918-1920.

Bresalier R S, Byrd J C, Tessler D, Lebel J, Koomen J, Hawke D, Half E, Liu K F, Mazurek N; Great Lakes-New England Clinical and Epidemiology Center of the Early Detection Research Network. (2004) A circulating ligand for galectin-3 is a haptoglobin-related glycoprotein elevated in individuals with colon cancer. Gastroenterology 127: 741-748.

Breslow R A, Sorkin J D, Frey C M, Kessler L G. (1997) Americans' knowledge of cancer risk and survival. Prev Med. 26: 170-177.

Brinkmann U, Brinkmann E, Pastan I. (1995a) Expression cloning of cDNAs that renders cancer cells resistant to *Pseudomonas* and diphtheria toxin and immunotoxins. Mol Med 1: 206-216.

Brinkmann U, Brinkmann E, Gallo M, Pastan I. (1995b) Cloning and characterization of a cellular apoptosis susceptibility gene, the human homologue to the yeast chromosome segregation gene CSE1. Proc Natl Acad Sci USA 92:10427-10431.

Chu D Z J, Erickson C A, Russell M P, Thompson C, Lang N P, Broadwater R J, Westbrook K C. (1991). Prognostic significance of carcinoembryonic antigen in colorectal carcinoma. Arch Surg 126: 314-316.

Fong S, García Vega G, León V. (1985) Carcinoembryonic antigen fraction in digestive cancer. Neoplasma 32: 199-208.

Go V L. (1976) Carcinoembryonic antigen: clinical application. Cancer 37: 562-566.

Gold P. Freedman S. O. (1965) Specific carcinoembryonic antigens of the human digestive system. J. Exp. Med. 122: 467-481.

Gupta A K, Brenner D E, Turgeon D K. (2008) Early detection of colon cancer: new tests on the horizon. Mol Diagn Ther. 12: 77-85.

Hammarström S. (1999) The carcinoembryonic antigen (CEA) family: structures, suggested functions and expression in normal and malignant tissues. *Sem. Cancer Biol.* 9: 67-81.

Holmbeck K, Bianco P, Yamada S, Birkedal-Hansen H. (2004) MT1-MMP: a tethered collagenase. J Cell Physiol 200: 11-19.

Hsu T C. (2006) Unusual elevation of CEA in a patient with history of colon cancer. Jpn J Clin Oncol. 36: 811-813.

Izaguirre M F, Vergara M N, Casco V H. (2006) CAS role in the brain apoptosis of Bufo arenarum induced by cypermethrin. Biocell 30: 309-320.

Jena B P. (2005) Molecular machinery and mechanism of cell secretion. Exp Biol Med (Maywood) 230: 307-319.

Jiang M C, Luo S F, Li L T, Lin C C, Du S Y, Lin C Y, Liao C F. (2007) Synergic CSE1L/CAS, TNFR-1, and p53 apoptotic pathways in combined interferon-gamma/adriamycin-induced apoptosis of Hep G2 hepatoma cells. J Exp Clin Cancer Res 26: 91-99.

Kutay U, Bischoff F R, Kostka S, Kraft R, Gorlich D. (1997) Export of importin alpha from the nucleus is mediated by a specific nuclear transport factor. Cell 90: 1061-1071.

Kwan J A, Schulze C J, Wang W, Leon H, Sariahmetoglu M, Sung M, Sawicka J, Sims D E, Sawicki G, Schulz R. (2004) Matrix metalloproteinase-2 (MMP-2) is present in the nucleus of cardiac myocytes and is capable of cleaving poly (ADP-ribose) polymerase (PARP) in vitro. FASEB J 18: 690-692.

Lassmann S, Tang L, Capanu M, Brabletz T, Schöpflin A, Zur Hausen A, Gonen M, Kemeny N, Shia J, Klimstra D, Werner M. (2007) Predictive molecular markers for colorectal cancer patients with resected liver metastasis and adjuvant chemotherapy. Gastroenterology. 133: 1831-1839.

Lee D C, Chua D T, Wei W I, Sham J S, Lau A S. (2007) Induction of matrix metalloproteinases by Epstein-Barr virus latent membrane protein 1 isolated from nasopharyngeal carcinoma. Biomed Pharmacother 61: 520-526.

Liao C F, Luo S F, Tsai C S, Tsao T Y, Chen S L, Jiang M C. (2008a) CAS enhances chemotherapeutic drug-induced p53 accumulation and apoptosis: use of CAS for high-sensitivity anticancer drug screening, Toxicol. Mech. Method. In press, DOI: 10.1080/15376510802428609.

Liao C F, Luo S F, Shen T Y, Lin C H, Chien J T, Du S Y, Jiang M C. (2008b) CSE1L/CAS, a microtubule-associated protein, inhibits taxol (paclitaxel)-induced apoptosis but enhances cancer cell apoptosis induced by various chemotherapeutic drugs. BMB Rep 41: 210-216.

Liao C F, Luo S F, Li L T, Lin C Y, Chen Y C, Jiang M C. (2008c) CSE1L/CAS, the cellular apoptosis susceptibility protein, enhances invasion and metastasis but not proliferation of cancer cells. J Exp Clin Cancer Res 27: 15. doi: 10.1186/1756-9966-27-15.

Moertel C G, Fleming T R, Macdonald J S, Haller D G, Laurie J A, Tangen C. (1993) An evaluation of the carcinoembryonic antigen (CEA) test for monitoring patients with resected colon cancer. JAMA. 270: 943-947.

Moser T L, Young T N, Rodriguez G C, Pizzo S V, Bast R C Jr, Stack M S. (1994) Secretion of extracellular matrix-degrading proteinases is increased in epithelial ovarian carcinoma. Int J Cancer 56: 552-559.

Nguyen M, Arkell J, Jackson C J. (1998) Active and tissue inhibitor of matrix metalloproteinase-free gelatinase B accumulates within human microvascular endothelial vesicles. J Biol Chem 273: 5400-5404.

Peiro G, Diebold J, Baretton G B, Kimmig R, Lohrs U. (2001) Cellular apoptosis susceptibility gene expression in endometrial carcinoma: correlation with Bcl-2, Bax, and caspase-3 expression and outcome. Int J Gynecol Pathol 20: 359-367.

Petricoin E F, Belluco C, Araujo R P, Liotta L A. (2006) The blood peptidome: a higher dimension of information content for cancer biomarker discovery. Nat Rev Cancer 6: 961-967.

Pickett J A, Edwardson J M. (2006) Compound exocytosis: mechanisms and functional significance. Traffic 7: 109-116.

Pieper-Bigelow C, Strocchi A, Levitt M D. (1990) Where does serum amylase come from and where does it go? Gastroenterol. Clin. North. Am. 19: 793-810.

Ransohoff D F, Martin C, Wiggins W S, Hitt B A, Keku T O, Galanko J A, Sandler R S. (2008) Assessment of serum proteomics to detect large colon adenomas. Cancer Epidemiol Biomarkers Prev. 17: 2188-2193.

Rex D K, Kahi C J, Levin B, Smith R A, Bond J H, Brooks D, Burt R W, Byers T, Fletcher R H, Hyman N, Johnson D, Kirk L, Lieberman D A, Levin T R, O'Brien M J, Simmang C, Thorson A G, Winawer S J; American Cancer Society; US Multi-Society Task Force on Colorectal Cancer. (2006) Guidelines for colonoscopy surveillance after cancer resection: a consensus update by the American Cancer Society and the US Multi-Society Task Force on Colorectal Cancer. Gastroenterology. 130: 1865-1871.

Rodrigues L R, Teixeira J A, Schmitt F L, Paulsson M, Lindmark-Månsson H. (2007) The role of osteopontin in tumor progression and metastasis in breast cancer. Cancer Epidemiol Biomarkers Prev 16: 1087-1097.

Saito N, Kameoka S. (2005) Serum laminin is an independent prognostic factor in colorectal cancer. Int J Colorectal Dis. 20: 238-244.

Savrin R A, Cooperman M, Martin E W Jr. (1979) Clinical application of carcinoembryonic antigen in patients with colorectal carcinoma. Dis Colon Rectum. 22: 211-215.

Scherf U, Pastan I, Willingham M C, Brinkmann U. (1996) The human CAS protein which is homologous to the CSE1 yeast chromosome segregation gene product is associated with microtubules and mitotic spindle. Proc Natl Acad Sci USA. April 2; 93(7):2670-2674.

Seiden-Long I M, Brown K R, Shih W, Wigle D A, Radulovich N, Jurisica I et al. (2006) Transcriptional targets of hepatocyte growth factor signalling and Ki-ras oncogene activation in colorectal cancer. Oncogene 25: 91-102.

Shields J D, Emmett M S, Dunn D B, Joory K D, Sage L M, Rigby H et al. (2007) Chemokine-mediated migration of melanoma cells towards lymphatics: a mechanism contributing to metastasis. Oncogene 26: 2997-3005.

Skates S J, Horick N K, Moy J M, Minihan A M, Seiden M V, Marks J R, Sluss P, Cramer D W. (2007) Pooling of case specimens to create standard serum sets for screening cancer biomarkers. Cancer Epidemiol Biomarkers Prev 16: 334-341.

Stein U, Arlt F, Walther W, Smith J, Waldman T, Harris E D, Mertins S D, Heizmann C W, Allard D, Birchmeier W, Schlag P M, Shoemaker R H. (2006) The metastasis-associated gene S100A4 is a novel target of beta-catenin/T-cell factor signaling in colon cancer. Gastroenterology. 131: 1486-1500.

Stetler-Stevenson W G, Aznavoorian S, Liotta L A. (1993) Tumor cell interactions with the extracellular matrix during invasion and metastasis. Annu Rev Cell Biol 9: 541-573.

Taraboletti G, Sonzogni L, Vergani V, Hosseini G, Ceruti R, Ghilardi C et al. (2000) Posttranscriptional stimulation of endothelial cell matrix metalloproteinases 2 and 1 by endothelioma cells. Exp Cell Res 258: 384-394.

Thomas C M, Sweep C G. (2001) Serum tumor markers: past, state of the art, and future. Int J Biol Markers 16: 73-86.

Thomson D M, Krupey J, Freedman S O, Gold P. (1969) The radioimmunoassay of circulating carcinoembryonic antigen of the human digestive system. Proc Natl Acad Sci USA 64: 161-167.

Wang H, Li M, Lin W, Wang W, Zhang Z, Rayburn E R, Lu J, Chen D, Yue X, Shen F, Jiang F, He J, Wei W, Zeng X, Zhang R. (2007) Extracellular activity of cyclic AMP-dependent protein kinase as a biomarker for human cancer detection: distribution characteristics in a normal population and cancer patients. Cancer Epidemiol Biomarkers Prev 16: 789-795.

Wellmann A, Flemming P, Behrens P, Wuppermann K, Lang H, Oldhafer K et al. (2001) High expression of the proliferation and apoptosis associated CSE1L/CAS gene in hepatitis and liver neoplasms: correlation with tumor progression. Int J Mol Med 7: 489-494.

Wellmann A, Krenacs L, Fest T, Scherf U, Pastan I, Raffeld M et al. (1997) Localization of the cell proliferation and apoptosis-associated CAS protein in lymphoid neoplasms. Am J Pathol 150: 25-30.

Zhang H, Chan D W. (2007) Cancer biomarker discovery in plasma using a tissue-targeted proteomic approach. Cancer Epidemiol Biomarkers Prev 16: 1915-1917.

Zigrino P, Löffek S, Mauch C. (2005) Tumor-stroma interactions: their role in the control of tumor cell invasion. Biochimie 87: 321-328.

What is claimed is:

1. A method of detecting metastasis of cancer in a body fluid from a mammal, the method comprising the steps of: (a) providing the body fluid from the mammal; and (b) measuring secreted cellular apoptosis susceptibility (CAS/CSE1L) protein level or secreted CAS/CSE1L polypeptide level using an immunological binding assay in the body fluid to screen or diagnose the metastatic cancer, wherein the metastatic cancer is detected when the secreted CAS/CSE1L protein level or secreted CAS/CSE1L polypeptide level in the body fluid is increased relative to the secreted CAS/CSE1L protein level or secreted CAS/CSE1L polypeptide level in the body fluid of an individual without cancer or in the body fluid of a patient with non-metastatic cancer.

2. The method of claim 1, wherein the mammal is a human.

3. The method of claim 1, wherein the measurement is to assay the level of secreted CAS/CSE1L protein.

4. The method of claim 1, wherein the immunological binding assay is ELISA.

5. The method of claim 1, wherein the immunological binding assay is immunoblotting.

6. The method of claim 1, wherein the immunological binding assay is flow cytometry.

7. The method of claim 1, wherein the body fluid is serum, urine, ascites, pleural effusion, or saliva.

8. The method of claim 1, wherein the metastatic cancer is metastasis of colorectal cancer, hypopharyngeal cancer, lung cancer, breast cancer, cervical cancer, lip cancer, or cholangiocarcinomas.

9. The method of claim 1, wherein the metastatic cancer is detected when the secreted CAS/CSE1L protein level or secreted CAS/CSE1L polypeptide level in the body fluid is increased relative to the secreted CAS/CSE1L protein level or secreted CAS/CSE1L polypeptide level in the body fluid of a patient with non-metastatic cancer.

10. The method of claim 1, wherein the metastatic cancer is detected when the secreted CAS/CSE1L protein level or secreted CAS/CSE1L polypeptide level in the body fluid is increased relative to the secreted CAS/CSE1L protein level or secreted CAS/CSE1L polypeptide level in the body fluid of an individual without cancer.

11. The method of claim 7, wherein the body fluid is serum or urine.

* * * * *